(12) United States Patent
Chapman et al.

(10) Patent No.: US 7,708,735 B2
(45) Date of Patent: May 4, 2010

(54) INCORPORATING RAPID COOLING IN TISSUE FUSION HEATING PROCESSES

(75) Inventors: Troy J. Chapman, Denver, CO (US); Curt D. Hammill, Erie, CO (US); Chelsea Shields, Portland, OR (US); David A. Schechter, Longmont, CO (US); Ronald J. Podhajsky, Boulder, CO (US)

(73) Assignee: Covidien AG, Neuhausen am Rheinfall (CH)

( * ) Notice: Subject to any disclaimer, the term of this patent is extended or adjusted under 35 U.S.C. 154(b) by 994 days.

(21) Appl. No.: 11/184,338

(22) Filed: Jul. 19, 2005

(65) Prior Publication Data
US 2006/0052778 A1 Mar. 9, 2006

Related U.S. Application Data

(63) Continuation-in-part of application No. PCT/US2004/013273, filed on Apr. 29, 2004.

(60) Provisional application No. 60/467,027, filed on May 1, 2003.

(51) Int. Cl.
*A61B 18/18* (2006.01)
(52) U.S. Cl. .......................................... 606/51; 606/52
(58) Field of Classification Search ............... 606/48–52
See application file for complete search history.

(56) References Cited

U.S. PATENT DOCUMENTS

| 371,664 A | 10/1887 | Brannan et al. |
|---|---|---|
| 702,472 A | 6/1902 | Pignolet |
| 728,883 A | 5/1903 | Downes |
| 1,586,645 A | 6/1926 | Bierman |
| 1,813,902 A | 7/1931 | Bovie |
| 1,822,330 A | 9/1931 | Ainslie |
| 1,852,542 A | 4/1932 | Sovatkin |
| 2,002,594 A | 5/1935 | Wappler et al. |

(Continued)

FOREIGN PATENT DOCUMENTS

CA 2104423 2/1994

(Continued)

OTHER PUBLICATIONS

Sigel et al. "The Mechanism of Blood Vessel Closure by High Frequency Electrocoagulation" Surgery Gynecology & Obstetrics, Oct. 1965 pp. 823-831.

(Continued)

*Primary Examiner*—Michael Peffley

(57) ABSTRACT

An electrode sealing assembly for use with an electrosurgical instrument for sealing tissue includes first and second jaw members which are movable from a first position in spaced relation relative to one another to at least one second position for grasping tissue. The jaw members include electrically conductive sealing plates designed to selectively transmit electrosurgical energy to tissue disposed between the sealing plates. The jaw members also include a thermoelectric cooling plate having a first surface in direct contact with an outer surface of the sealing plate. The thermoelectric cooling plate includes first and second electrical connections on opposite sides of the jaw member. The first connection is configured to selectively transmit a first electrical potential and the second connection is configured to selectively transmit a second electrical potential such that heat generated by the sealing plates is transferred away from the tissue via the thermoelectric cooling plate.

8 Claims, 17 Drawing Sheets

U.S. PATENT DOCUMENTS

| | | |
|---|---|---|
| 2,011,169 A | 8/1935 | Wappler |
| 2,031,682 A | 2/1936 | Wappler et al. |
| 2,054,149 A | 9/1936 | Wappler |
| 2,176,479 A | 10/1939 | Willis |
| 2,279,753 A | 4/1942 | Knopp |
| 2,305,156 A | 12/1942 | Grubel |
| 2,327,353 A | 8/1943 | Karle |
| 2,632,661 A | 3/1953 | Cristofv |
| 2,668,538 A | 2/1954 | Baker |
| 2,796,065 A | 6/1957 | Kapp |
| 3,073,311 A | 1/1963 | Tibbs et al. |
| 3,372,288 A | 3/1968 | Wigington |
| 3,459,187 A | 8/1969 | Pallotta |
| 3,643,663 A | 2/1972 | Sutter |
| 3,648,001 A | 3/1972 | Anderson et al. |
| 3,651,811 A | 3/1972 | Hildebrandt et al. |
| 3,678,229 A | 7/1972 | Osika |
| 3,720,896 A | 3/1973 | Beierlein |
| 3,763,726 A | 10/1973 | Hildebrand |
| 3,779,918 A | 12/1973 | Ikeda et al. |
| 3,801,766 A | 4/1974 | Morrison, Jr. |
| 3,862,630 A | 1/1975 | Balamuth |
| 3,863,339 A | 2/1975 | Reaney et al. |
| 3,866,610 A | 2/1975 | Kletschka |
| 3,911,766 A | 10/1975 | Fridolph et al. |
| 3,920,021 A | 11/1975 | Hiltebrandt |
| 3,921,641 A | 11/1975 | Hulka |
| 3,938,527 A | 2/1976 | Rioux et al. |
| 3,952,749 A | 4/1976 | Fridolph et al. |
| 3,970,088 A | 7/1976 | Morrison |
| 3,987,795 A | 10/1976 | Morrison |
| 4,005,714 A | 2/1977 | Hiltebrandt |
| 4,016,881 A | 4/1977 | Rioux et al. |
| 4,041,952 A | 8/1977 | Morrison, Jr. et al. |
| 4,043,342 A | 8/1977 | Morrison, Jr. |
| 4,074,718 A | 2/1978 | Morrison, Jr. |
| 4,076,028 A | 2/1978 | Simmons |
| 4,080,820 A | 3/1978 | Allen |
| 4,088,134 A | 5/1978 | Mazzariello |
| 4,112,950 A | 9/1978 | Pike |
| 4,127,222 A | 11/1978 | Adams |
| 4,128,099 A | 12/1978 | Bauer |
| 4,165,746 A | 8/1979 | Burgin |
| 4,187,420 A | 2/1980 | Piber |
| 4,233,734 A | 11/1980 | Bies |
| 4,236,470 A | 12/1980 | Stenson |
| 4,300,564 A | 11/1981 | Furihata |
| 4,311,145 A | 1/1982 | Esty et al. |
| D263,020 S | 2/1982 | Rau, III |
| 4,370,980 A | 2/1983 | Lottick |
| 4,375,218 A | 3/1983 | DiGeronimo |
| 4,416,276 A | 11/1983 | Newton et al. |
| 4,418,692 A | 12/1983 | Guay |
| 4,443,935 A | 4/1984 | Zamba et al. |
| 4,452,246 A | 6/1984 | Bader et al. |
| 4,470,786 A | 9/1984 | Sano et al. |
| 4,492,231 A | 1/1985 | Auth |
| 4,493,320 A | 1/1985 | Treat |
| 4,503,855 A | 3/1985 | Maslanka |
| 4,506,669 A | 3/1985 | Blake, III |
| 4,509,518 A | 4/1985 | McGarry et al. |
| 4,552,143 A | 11/1985 | Lottick |
| 4,574,804 A | 3/1986 | Kurwa |
| 4,597,379 A | 7/1986 | Kihn et al. |
| 4,600,007 A | 7/1986 | Lahodny et al. |
| 4,624,254 A | 11/1986 | McGarry et al. |
| 4,655,215 A | 4/1987 | Pike |
| 4,657,016 A | 4/1987 | Garito et al. |
| 4,662,372 A | 5/1987 | Sharkany et al. |
| 4,671,274 A | 6/1987 | Sorochenko |
| 4,685,459 A | 8/1987 | Xoch et al. |
| 4,733,662 A | 3/1988 | DeSatnick et al. |
| D295,893 S | 5/1988 | Sharkany et al. |
| D295,894 S | 5/1988 | Sharkany et al. |
| 4,754,892 A | 7/1988 | Retief |
| 4,763,669 A | 8/1988 | Jaeger |
| 4,827,929 A | 5/1989 | Hodge |
| 4,829,313 A | 5/1989 | Taggart |
| 4,846,171 A | 7/1989 | Kauphusman et al. |
| 4,887,612 A | 12/1989 | Esser et al. |
| 4,938,761 A | 7/1990 | Ensslin |
| 4,947,009 A | 8/1990 | Osika et al. |
| 4,985,030 A | 1/1991 | Melzer et al. |
| 5,007,908 A | 4/1991 | Rydell |
| 5,026,370 A | 6/1991 | Lottick |
| 5,026,371 A | 6/1991 | Rydell et al. |
| 5,035,695 A | 7/1991 | Weber, Jr. et al. |
| 5,037,433 A | 8/1991 | Wilk et al. |
| 5,042,707 A | 8/1991 | Taheri |
| 5,047,046 A | 9/1991 | Bodoia |
| 5,078,716 A | 1/1992 | Doll |
| 5,084,057 A | 1/1992 | Green et al. |
| 5,085,659 A | 2/1992 | Rydell |
| 5,099,840 A | 3/1992 | Goble et al. |
| 5,100,430 A | 3/1992 | Avellanet et al. |
| 5,108,392 A | 4/1992 | Spingler |
| 5,112,343 A | 5/1992 | Thornton |
| 5,116,332 A | 5/1992 | Lottick |
| 5,147,357 A | 9/1992 | Rose et al. |
| 5,151,102 A | 9/1992 | Xamiyama et al. |
| 5,151,978 A | 9/1992 | Bronikowski et al. |
| 5,176,695 A | 1/1993 | Dulebohn |
| 5,190,541 A | 3/1993 | Abele et al. |
| 5,196,009 A | 3/1993 | Kirwan, Jr. |
| 5,197,964 A | 3/1993 | Parins |
| 5,209,747 A | 5/1993 | Knoepfler |
| 5,211,655 A | 5/1993 | Hasson |
| 5,215,101 A | 6/1993 | Jacobs et al. |
| 5,217,457 A | 6/1993 | Delahuerga et al. |
| 5,217,458 A | 6/1993 | Parins |
| 5,217,460 A | 6/1993 | Knoepfler |
| 5,244,462 A | 9/1993 | Delahuerga et al. |
| 5,250,047 A | 10/1993 | Rydell |
| 5,250,063 A | 10/1993 | Abidin et al. |
| 5,258,001 A | 11/1993 | Corman |
| 5,258,006 A | 11/1993 | Rydell et al. |
| 5,261,918 A | 11/1993 | Phillips et al. |
| 5,275,615 A | 1/1994 | Rose |
| 5,277,201 A | 1/1994 | Stern |
| 5,282,799 A | 2/1994 | Rydell |
| 5,282,800 A | 2/1994 | Foshee et al. |
| 5,282,826 A | 2/1994 | Quadri |
| 5,290,286 A | 3/1994 | Parins |
| 5,300,082 A | 4/1994 | Sharpe et al. |
| 5,304,203 A | 4/1994 | El-Mallawany et al. |
| 5,308,353 A | 5/1994 | Beurrier |
| 5,308,357 A | 5/1994 | Lichtman |
| 5,313,027 A | 5/1994 | Inoue et al. |
| 5,314,445 A | 5/1994 | Degwitz et al. |
| 5,318,589 A | 6/1994 | Lichtman |
| 5,324,289 A | 6/1994 | Eggers |
| D348,930 S | 7/1994 | Olson |
| 5,326,806 A | 7/1994 | Yokoshima et al. |
| 5,330,471 A | 7/1994 | Eggers |
| 5,330,502 A | 7/1994 | Hassler et al. |
| 5,334,183 A | 8/1994 | Wuchinich |
| 5,334,215 A | 8/1994 | Chen |
| 5,336,220 A | 8/1994 | Ryan et al. |
| 5,336,221 A | 8/1994 | Anderson |
| 5,342,359 A | 8/1994 | Rydell |
| 5,342,381 A | 8/1994 | Tidemand |
| 5,342,393 A | 8/1994 | Stack |
| 5,344,424 A | 9/1994 | Roberts et al. |
| 5,350,391 A | 9/1994 | Iacovelli |

| Patent No. | Date | Inventor |
|---|---|---|
| 5,352,222 A | 10/1994 | Rydell |
| 5,354,271 A | 10/1994 | Voda |
| 5,356,408 A | 10/1994 | Rydell |
| 5,366,477 A | 11/1994 | LeMarie, III et al. |
| 5,368,600 A | 11/1994 | Failla et al. |
| 5,374,277 A | 12/1994 | Hassler |
| 5,376,089 A | 12/1994 | Smith |
| 5,383,875 A | 1/1995 | Bays et al. |
| 5,383,897 A | 1/1995 | Wholey |
| 5,389,098 A | 2/1995 | Tsuruta et al. |
| 5,389,103 A | 2/1995 | Melzer et al. |
| 5,389,104 A | 2/1995 | Hahnen et al. |
| 5,391,166 A | 2/1995 | Eggers |
| 5,391,183 A | 2/1995 | Janzen et al. |
| 5,396,900 A | 3/1995 | Slater et al. |
| 5,403,312 A | 4/1995 | Yates et al. |
| 5,403,342 A | 4/1995 | Tovey et al. |
| 5,405,344 A | 4/1995 | Williamson et al. |
| 5,409,763 A | 4/1995 | Serizawa et al. |
| 5,411,519 A | 5/1995 | Tovey et al. |
| 5,411,520 A | 5/1995 | Nash et al. |
| 5,413,571 A | 5/1995 | Katsaros et al. |
| 5,415,656 A | 5/1995 | Tihon et al. |
| 5,415,657 A | 5/1995 | Taymor-Luria |
| 5,422,567 A | 6/1995 | Matsunaga |
| 5,423,810 A | 6/1995 | Goble et al. |
| 5,425,690 A | 6/1995 | Chang |
| 5,425,739 A | 6/1995 | Jessen |
| 5,429,616 A | 7/1995 | Schaffer |
| 5,431,672 A | 7/1995 | Cote et al. |
| 5,431,674 A | 7/1995 | Basile et al. |
| 5,437,292 A | 8/1995 | Kipshidze et al. |
| 5,438,302 A | 8/1995 | Goble |
| 5,439,478 A | 8/1995 | Palmer |
| 5,441,517 A | 8/1995 | Kensey et al. |
| 5,443,463 A | 8/1995 | Stern et al. |
| 5,443,464 A | 8/1995 | Russell et al. |
| 5,443,480 A | 8/1995 | Jacobs et al. |
| 5,445,638 A | 8/1995 | Rydell et al. |
| 5,445,658 A | 8/1995 | Durrfeld et al. |
| 5,449,480 A | 9/1995 | Kuriya et al. |
| 5,451,224 A | 9/1995 | Goble et al. |
| 5,454,823 A | 10/1995 | Richardson et al. |
| 5,454,827 A | 10/1995 | Aust et al. |
| 5,456,684 A | 10/1995 | Schmidt et al. |
| 5,458,598 A | 10/1995 | Feinberg et al. |
| 5,460,629 A | 10/1995 | Shlain et al. |
| 5,461,765 A | 10/1995 | Linden et al. |
| 5,462,546 A | 10/1995 | Rydell |
| 5,472,442 A | 12/1995 | Klicek |
| 5,472,443 A | 12/1995 | Cordis et al. |
| 5,478,351 A | 12/1995 | Meade et al. |
| 5,480,406 A | 1/1996 | Nolan et al. |
| 5,480,409 A | 1/1996 | Riza |
| 5,484,436 A | 1/1996 | Eggers et al. |
| 5,496,312 A | 3/1996 | Klicek |
| 5,496,317 A | 3/1996 | Goble et al. |
| 5,496,347 A | 3/1996 | Hashiguchi et al. |
| 5,499,997 A | 3/1996 | Sharpe et al. |
| 5,509,922 A | 4/1996 | Aranyi et al. |
| 5,514,134 A | 5/1996 | Rydell et al. |
| 5,527,313 A | 6/1996 | Scott et al. |
| 5,528,833 A | 6/1996 | Sakuma |
| 5,529,067 A * | 6/1996 | Larsen et al. ............... 600/374 |
| 5,531,744 A | 7/1996 | Nardella et al. |
| 5,536,251 A | 7/1996 | Evard et al. |
| 5,540,684 A | 7/1996 | Hassler, Jr. |
| 5,540,685 A | 7/1996 | Parins et al. |
| 5,540,706 A | 7/1996 | Aust et al. |
| 5,540,715 A | 7/1996 | Katsaros et al. |
| 5,542,945 A | 8/1996 | Fritzsch |
| 5,558,671 A | 9/1996 | Yates |
| 5,558,672 A | 9/1996 | Edwards et al. |
| 5,562,619 A | 10/1996 | Mirarchi et al. |
| 5,562,699 A | 10/1996 | Heimberger et al. |
| 5,562,720 A | 10/1996 | Stern et al. |
| 5,564,615 A | 10/1996 | Bishop et al. |
| 5,569,241 A | 10/1996 | Edwardds |
| 5,569,243 A | 10/1996 | Kortenbach et al. |
| 5,571,100 A | 11/1996 | Goble et al. |
| 5,573,424 A | 11/1996 | Poppe |
| 5,573,534 A | 11/1996 | Stone |
| 5,573,535 A | 11/1996 | Viklund |
| 5,575,799 A | 11/1996 | Bolanos et al. |
| 5,575,805 A | 11/1996 | Li |
| 5,578,052 A | 11/1996 | Koros et al. |
| 5,579,781 A | 12/1996 | Cooke |
| 5,582,611 A | 12/1996 | Tsukagoshi et al. |
| 5,582,617 A | 12/1996 | Klieman et al. |
| 5,585,896 A | 12/1996 | Yamazaki et al. |
| 5,590,570 A | 1/1997 | LeMaire, III et al. |
| 5,591,181 A | 1/1997 | Stone et al. |
| 5,597,107 A | 1/1997 | Knodel et al. |
| 5,601,224 A | 2/1997 | Bishop et al. |
| 5,601,641 A | 2/1997 | Stephens |
| 5,603,711 A | 2/1997 | Parins et al. |
| 5,603,723 A | 2/1997 | Aranyi et al. |
| 5,611,798 A | 3/1997 | Eggers |
| 5,611,808 A | 3/1997 | Hossain et al. |
| 5,611,813 A | 3/1997 | Lichtman |
| 5,620,415 A | 4/1997 | Lucey et al. |
| 5,620,453 A | 4/1997 | Nallakrishnan |
| 5,620,459 A | 4/1997 | Lichtman |
| 5,624,452 A | 4/1997 | Yates |
| 5,626,578 A | 5/1997 | Tihon |
| 5,626,609 A | 5/1997 | Zvenyatsky et al. |
| 5,630,833 A | 5/1997 | Katsaros et al. |
| 5,637,110 A | 6/1997 | Pennybacker et al. |
| 5,638,003 A | 6/1997 | Hall |
| 5,643,294 A | 7/1997 | Tovey et al. |
| 5,647,869 A | 7/1997 | Goble et al. |
| 5,647,871 A * | 7/1997 | Levine et al. ................. 606/45 |
| 5,649,959 A | 7/1997 | Hannam et al. |
| 5,655,650 A | 8/1997 | Naitou |
| 5,658,281 A | 8/1997 | Heard |
| D384,413 S | 9/1997 | Zlock et al. |
| 5,662,667 A | 9/1997 | Knodel |
| 5,665,100 A | 9/1997 | Yoon |
| 5,667,526 A | 9/1997 | Levin |
| 5,674,220 A | 10/1997 | Fox et al. |
| 5,674,229 A | 10/1997 | Tovey et al. |
| 5,681,282 A | 10/1997 | Eggers et al. |
| 5,688,270 A | 11/1997 | Yates et al. |
| 5,690,652 A | 11/1997 | Wurster et al. |
| 5,690,653 A | 11/1997 | Richardson et al. |
| 5,693,051 A | 12/1997 | Schulze et al. |
| 5,693,920 A | 12/1997 | Maeda |
| 5,695,522 A | 12/1997 | LeMaire, III et al. |
| 5,700,261 A | 12/1997 | Brinkerhoff |
| 5,700,270 A | 12/1997 | Peyser et al. |
| 5,702,390 A | 12/1997 | Austin et al. |
| 5,707,369 A | 1/1998 | Vaitekunas et al. |
| 5,709,680 A | 1/1998 | Yates et al. |
| 5,716,366 A | 2/1998 | Yates |
| 5,720,744 A | 2/1998 | Eggleston et al. |
| 5,722,421 A | 3/1998 | Francese et al. |
| 5,725,536 A | 3/1998 | Oberlin et al. |
| 5,727,428 A | 3/1998 | LeMaire, III et al. |
| 5,735,848 A | 4/1998 | Yates et al. |
| 5,743,906 A | 4/1998 | Parins et al. |
| 5,752,973 A | 5/1998 | Kieturakis |
| 5,755,717 A | 5/1998 | Yates et al. |
| 5,759,188 A | 6/1998 | Yoon |
| 5,766,130 A | 6/1998 | Selmonosky |
| 5,766,166 A | 6/1998 | Hooven |
| 5,766,170 A | 6/1998 | Eggers |

| | | | | | |
|---|---|---|---|---|---|
| 5,766,196 A | 6/1998 | Griffiths | 5,984,932 A | 11/1999 | Yoon |
| 5,769,849 A | 6/1998 | Eggers | 5,984,938 A | 11/1999 | Yoon |
| 5,772,655 A | 6/1998 | Bauer et al. | 5,989,277 A | 11/1999 | LeMaire, III et al. |
| 5,772,670 A | 6/1998 | Brosa | 5,993,466 A | 11/1999 | Yoon |
| 5,776,128 A | 7/1998 | Eggers | 5,993,467 A | 11/1999 | Yoon |
| 5,776,130 A | 7/1998 | Buysse et al. | 5,997,565 A | 12/1999 | Inoue |
| 5,779,646 A | 7/1998 | Koblish et al. | 6,004,332 A | 12/1999 | Yoon et al. |
| 5,779,701 A | 7/1998 | McBrayer et al. | 6,004,335 A | 12/1999 | Vaitekunas et al. |
| H1745 H | 8/1998 | Paraschac | 6,010,516 A | 1/2000 | Hulka et al. |
| 5,792,137 A | 8/1998 | Carr et al. | 6,017,358 A | 1/2000 | Yoon et al. |
| 5,792,165 A | 8/1998 | Klieman et al. | 6,021,693 A | 2/2000 | Feng-Sing |
| 5,792,177 A | 8/1998 | Kaseda | 6,024,741 A | 2/2000 | Williamson et al. |
| 5,797,537 A | 8/1998 | Oberlin et al. | 6,024,743 A | 2/2000 | Edwards |
| 5,797,927 A | 8/1998 | Yoon | 6,024,744 A | 2/2000 | Kese et al. |
| 5,797,938 A | 8/1998 | Paraschac et al. | 6,027,522 A | 2/2000 | Palmer |
| 5,797,941 A | 8/1998 | Schulze et al. | 6,030,384 A | 2/2000 | Nezhat |
| 5,797,958 A | 8/1998 | Yoon | 6,033,399 A | 3/2000 | Gines |
| 5,800,449 A | 9/1998 | Wales | 6,039,733 A | 3/2000 | Buysse et al. |
| 5,807,393 A | 9/1998 | Williamson, IV et al. | 6,041,679 A | 3/2000 | Slater et al. |
| 5,810,764 A | 9/1998 | Eggers et al. | 6,050,996 A | 4/2000 | Schmaltz et al. |
| 5,810,805 A | 9/1998 | Sutcu et al. | 6,053,914 A | 4/2000 | Eggers et al. |
| 5,810,808 A | 9/1998 | Eggers | 6,053,933 A | 4/2000 | Balazs et al. |
| 5,810,811 A | 9/1998 | Yates et al. | D424,694 S | 5/2000 | Tetzlaff et al. |
| 5,810,877 A | 9/1998 | Roth et al. | D425,201 S | 5/2000 | Tetzlaff et al. |
| 5,814,043 A | 9/1998 | Shapeton | 6,059,782 A | 5/2000 | Novak et al. |
| 5,814,054 A | 9/1998 | Kortenbach et al. | 6,066,139 A | 5/2000 | Ryan et al. |
| 5,817,093 A | 10/1998 | Williamson, IV et al. | 6,074,386 A | 6/2000 | Goble et al. |
| 5,817,119 A | 10/1998 | Klieman et al. | 6,077,287 A | 6/2000 | Taylor et al. |
| 5,820,630 A | 10/1998 | Lind | 6,080,180 A | 6/2000 | Yoon et al. |
| 5,824,978 A | 10/1998 | Karasik et al. | RE36,795 E | 7/2000 | Rydell |
| 5,827,271 A | 10/1998 | Buysse et al. | 6,083,223 A | 7/2000 | Baker |
| 5,827,279 A | 10/1998 | Hughett et al. | 6,086,586 A | 7/2000 | Hooven |
| 5,827,281 A | 10/1998 | Levin | 6,086,601 A | 7/2000 | Yoon |
| 5,827,323 A | 10/1998 | Klieman et al. | 6,090,107 A | 7/2000 | Borgmeier et al. |
| 5,827,548 A | 10/1998 | Lavallee et al. | 6,096,037 A | 8/2000 | Mulier et al. |
| 5,833,690 A | 11/1998 | Yates et al. | 6,099,550 A | 8/2000 | Yoon |
| 5,843,080 A | 12/1998 | Fleenor et al. | 6,102,909 A | 8/2000 | Chen et al. |
| 5,849,022 A | 12/1998 | Sakashita et al. | 6,106,542 A | 8/2000 | Toybin et al. |
| 5,853,412 A | 12/1998 | Mayenberger | 6,110,171 A | 8/2000 | Rydell |
| 5,859,527 A | 1/1999 | Cook | 6,113,596 A | 9/2000 | Hooven et al. |
| 5,860,976 A | 1/1999 | Billings et al. | 6,113,598 A | 9/2000 | Baker |
| 5,876,401 A | 3/1999 | Schulze et al. | 6,117,158 A | 9/2000 | Measamer et al. |
| 5,876,412 A | 3/1999 | Piraka | 6,122,549 A | 9/2000 | Sharkey et al. |
| 5,882,567 A | 3/1999 | Cavallaro et al. | 6,123,701 A | 9/2000 | Nezhat |
| 5,891,141 A | 4/1999 | Rydell | H1904 H | 10/2000 | Yates et al. |
| 5,891,142 A | 4/1999 | Eggers et al. | 6,126,658 A | 10/2000 | Baker |
| 5,893,863 A | 4/1999 | Yoon | 6,126,665 A | 10/2000 | Yoon |
| 5,893,875 A | 4/1999 | O'Connor et al. | 6,139,563 A | 10/2000 | Cosgrove, III et al. |
| 5,893,877 A | 4/1999 | Gampp, Jr. et al. | 6,143,005 A | 11/2000 | Yoon et al. |
| 5,897,563 A | 4/1999 | Yoon et al. | 6,152,923 A | 11/2000 | Ryan |
| 5,902,301 A | 5/1999 | Olig | 6,162,220 A | 12/2000 | Nezhat |
| 5,906,630 A | 5/1999 | Anderhub et al. | 6,171,316 B1 | 1/2001 | Kovac et al. |
| 5,908,420 A | 6/1999 | Parins et al. | 6,174,309 B1 | 1/2001 | Wrublewski et al. |
| 5,908,432 A | 6/1999 | Pan | 6,178,628 B1 | 1/2001 | Clemens et al. |
| 5,911,719 A | 6/1999 | Eggers | 6,179,834 B1 | 1/2001 | Buysse et al. |
| 5,913,874 A | 6/1999 | Berns et al. | 6,179,837 B1 | 1/2001 | Hooven |
| 5,921,916 A | 7/1999 | Aeikens et al. | 6,183,467 B1 | 2/2001 | Shapeton et al. |
| 5,921,984 A | 7/1999 | Sutcu et al. | 6,187,003 B1 | 2/2001 | Buysse et al. |
| 5,925,043 A | 7/1999 | Kumar et al. | 6,190,386 B1 | 2/2001 | Rydell |
| 5,928,136 A | 7/1999 | Barry | 6,190,400 B1 | 2/2001 | Vandemoer et al. |
| 5,935,126 A | 8/1999 | Riza | 6,193,718 B1 | 2/2001 | Kortenbach et al. |
| 5,941,869 A | 8/1999 | Patterson et al. | 6,206,876 B1 | 3/2001 | Levine et al. |
| 5,944,718 A | 8/1999 | Dafforn et al. | 6,206,877 B1 | 3/2001 | Kese et al. |
| 5,951,546 A * | 9/1999 | Lorentzen .................. 606/41 | 6,206,893 B1 | 3/2001 | Klein et al. |
| 5,951,549 A | 9/1999 | Richardson et al. | 6,214,028 B1 | 4/2001 | Yoon et al. |
| 5,954,720 A | 9/1999 | Wilson et al. | 6,217,602 B1 | 4/2001 | Redmon |
| 5,954,731 A | 9/1999 | Yoon | 6,217,615 B1 | 4/2001 | Sioshansi et al. |
| 5,954,733 A | 9/1999 | Yoon | 6,221,039 B1 | 4/2001 | Durgin et al. |
| 5,957,923 A | 9/1999 | Hahnen et al. | 6,223,100 B1 | 4/2001 | Green |
| 5,957,937 A | 9/1999 | Yoon | 6,224,593 B1 | 5/2001 | Ryan et al. |
| 5,960,544 A | 10/1999 | Beyers | 6,224,614 B1 | 5/2001 | Yoon |
| 5,964,758 A | 10/1999 | Dresden | 6,228,080 B1 | 5/2001 | Gines |
| 5,976,132 A | 11/1999 | Morris | 6,228,083 B1 | 5/2001 | Lands et al. |

| | | |
|---|---|---|
| 6,248,124 B1 | 6/2001 | Pedros et al. |
| 6,248,944 B1 | 6/2001 | Ito |
| 6,261,307 B1 | 7/2001 | Yoon et al. |
| 6,267,761 B1 | 7/2001 | Ryan |
| 6,270,497 B1 | 8/2001 | Sekino et al. |
| 6,270,508 B1 | 8/2001 | Klieman et al. |
| 6,273,887 B1 | 8/2001 | Yamauchi et al. |
| 6,277,117 B1 | 8/2001 | Tetzlaff et al. |
| 6,280,458 B1 | 8/2001 | Boche et al. |
| 6,283,961 B1 | 9/2001 | Underwood et al. |
| D449,886 S | 10/2001 | Tetzlaff et al. |
| 6,298,550 B1 | 10/2001 | Kirwan |
| 6,302,424 B1 | 10/2001 | Gisinger et al. |
| 6,319,262 B1 | 11/2001 | Bates et al. |
| 6,319,451 B1 | 11/2001 | Brune |
| 6,322,561 B1 | 11/2001 | Eggers et al. |
| 6,322,580 B1 | 11/2001 | Kanner |
| 6,325,795 B1 | 12/2001 | Lindemann et al. |
| 6,334,860 B1 | 1/2002 | Dorn |
| 6,334,861 B1 | 1/2002 | Chandler et al. |
| 6,345,532 B1 | 2/2002 | Coudray et al. |
| 6,350,264 B1 | 2/2002 | Hooven |
| 6,352,536 B1 | 3/2002 | Buysse et al. |
| 6,358,249 B1 | 3/2002 | Chen et al. |
| 6,358,259 B1 | 3/2002 | Swain et al. |
| 6,358,268 B1 | 3/2002 | Hunt et al. |
| 6,364,879 B1 | 4/2002 | Chen et al. |
| D457,958 S | 5/2002 | Dycus et al. |
| D457,959 S | 5/2002 | Tetzlaff et al. |
| 6,391,035 B1 | 5/2002 | Appleby et al. |
| 6,398,779 B1 | 6/2002 | Buysse et al. |
| 6,402,747 B1 | 6/2002 | Lindemann et al. |
| 6,409,728 B1 | 6/2002 | Ehr et al. |
| H2037 H | 7/2002 | Yates et al. |
| 6,419,675 B1 | 7/2002 | Gallo, Sr. |
| 6,425,896 B1 | 7/2002 | Baltschun et al. |
| 6,432,112 B2 | 8/2002 | Brock et al. |
| 6,440,144 B1 | 8/2002 | Bacher |
| 6,443,952 B1 | 9/2002 | Mulier et al. |
| 6,443,970 B1 | 9/2002 | Schulze et al. |
| 6,451,018 B1 | 9/2002 | Lands et al. |
| 6,458,125 B1 | 10/2002 | Cosmescu |
| 6,458,128 B1 | 10/2002 | Schulze |
| 6,458,130 B1 | 10/2002 | Frazier et al. |
| 6,461,352 B2 | 10/2002 | Morgan et al. |
| 6,461,368 B2 | 10/2002 | Fogarty et al. |
| 6,464,701 B1 | 10/2002 | Hooven et al. |
| 6,464,702 B2 | 10/2002 | Schulze et al. |
| 6,464,704 B2 | 10/2002 | Schmaltz et al. |
| 6,485,489 B2 | 11/2002 | Teirstein et al. |
| 6,494,888 B1 | 12/2002 | Laufer et al. |
| 6,500,176 B1 * | 12/2002 | Truckai et al. ............... 606/51 |
| 6,506,196 B1 | 1/2003 | Laufer |
| 6,508,815 B1 | 1/2003 | Strul et al. |
| 6,511,480 B1 | 1/2003 | Tetzlaff et al. |
| 6,514,215 B1 | 2/2003 | Ouchi |
| 6,514,252 B2 | 2/2003 | Nezhat et al. |
| 6,517,539 B1 | 2/2003 | Smith et al. |
| 6,527,771 B1 | 3/2003 | Weadock et al. |
| 6,533,784 B2 | 3/2003 | Truckai et al. |
| 6,545,239 B2 | 4/2003 | Spedale et al. |
| 6,558,385 B1 | 5/2003 | McClurken et al. |
| 6,562,037 B2 | 5/2003 | Paton et al. |
| 6,569,105 B1 | 5/2003 | Kortenbach et al. |
| 6,582,450 B2 | 6/2003 | Ouchi |
| 6,585,735 B1 | 7/2003 | Frazier et al. |
| 6,602,252 B2 | 8/2003 | Mollenauer |
| 6,605,790 B2 | 8/2003 | Yoshida |
| 6,616,658 B2 | 9/2003 | Ineson |
| 6,616,661 B2 | 9/2003 | Wellman et al. |
| 6,620,161 B2 | 9/2003 | Schulze et al. |
| 6,620,184 B2 | 9/2003 | de Laforcade et al. |
| 6,626,901 B1 | 9/2003 | Treat et al. |
| 6,638,287 B2 | 10/2003 | Danitz et al. |
| 6,641,595 B1 | 11/2003 | Moran et al. |
| 6,652,514 B2 | 11/2003 | Ellman et al. |
| 6,656,175 B2 | 12/2003 | Francischelli et al. |
| 6,656,177 B2 | 12/2003 | Truckai et al. |
| 6,660,072 B2 | 12/2003 | Chatterjee |
| 6,663,639 B1 | 12/2003 | Laufer et al. |
| 6,663,641 B1 | 12/2003 | Kovac et al. |
| 6,666,854 B1 | 12/2003 | Lange |
| 6,669,696 B2 | 12/2003 | Bacher et al. |
| 6,673,092 B1 | 1/2004 | Bacher |
| 6,676,660 B2 | 1/2004 | Wampler et al. |
| 6,676,676 B2 | 1/2004 | Danitz et al. |
| 6,679,882 B1 | 1/2004 | Kornerup |
| 6,682,527 B2 | 1/2004 | Strul |
| 6,682,528 B2 | 1/2004 | Frazier et al. |
| 6,685,724 B1 | 2/2004 | Haluck |
| 6,689,131 B2 | 2/2004 | McClurken |
| 6,692,445 B2 | 2/2004 | Roberts et al. |
| 6,693,246 B1 | 2/2004 | Rudolph et al. |
| 6,695,840 B2 | 2/2004 | Schulze |
| 6,702,810 B2 | 3/2004 | McClurken et al. |
| 6,723,092 B2 | 4/2004 | Brown et al. |
| 6,726,068 B2 | 4/2004 | Miller |
| 6,726,686 B2 | 4/2004 | Buysse et al. |
| 6,726,694 B2 | 4/2004 | Blatter et al. |
| 6,733,498 B2 | 5/2004 | Paton et al. |
| 6,736,813 B2 | 5/2004 | Yamauchi et al. |
| 6,743,229 B2 | 6/2004 | Buysse et al. |
| 6,743,230 B2 | 6/2004 | Lutze et al. |
| 6,743,239 B1 | 6/2004 | Kuehn et al. |
| 6,743,240 B2 | 6/2004 | Smith et al. |
| 6,755,843 B2 | 6/2004 | Chung et al. |
| 6,756,553 B1 | 6/2004 | Yamaguchi et al. |
| 6,757,977 B2 | 7/2004 | Dambal et al. |
| D493,888 S | 8/2004 | Reschke |
| 6,770,072 B2 | 8/2004 | Truckai et al. |
| 6,773,409 B2 | 8/2004 | Truckai et al. |
| 6,773,432 B1 | 8/2004 | Clayman et al. |
| 6,773,434 B2 | 8/2004 | Ciarrocca |
| 6,773,441 B1 | 8/2004 | Laufer et al. |
| 6,775,575 B2 | 8/2004 | Bommannan et al. |
| 6,776,780 B2 | 8/2004 | Mulier et al. |
| 6,786,905 B2 | 9/2004 | Swanson et al. |
| 6,790,217 B2 | 9/2004 | Schulze et al. |
| 6,796,981 B2 | 9/2004 | Wham et al. |
| D496,997 S | 10/2004 | Dycus et al. |
| 6,800,825 B1 | 10/2004 | Sasaki et al. |
| 6,802,843 B2 | 10/2004 | Truckai et al. |
| 6,808,525 B2 | 10/2004 | Latterell et al. |
| D499,181 S | 11/2004 | Dycus et al. |
| 6,818,000 B2 | 11/2004 | Muller et al. |
| 6,821,285 B2 | 11/2004 | Laufer et al. |
| 6,835,200 B2 | 12/2004 | Laufer et al. |
| 6,857,357 B2 | 2/2005 | Fujii |
| 6,860,880 B2 | 3/2005 | Treat et al. |
| 6,887,240 B1 | 5/2005 | Lands et al. |
| 6,889,116 B2 | 5/2005 | Jinno |
| 6,914,201 B2 | 7/2005 | Van Vooren et al. |
| 6,926,716 B2 | 8/2005 | Baker et al. |
| 6,929,644 B2 | 8/2005 | Truckai et al. |
| 6,932,810 B2 | 8/2005 | Ryan |
| 6,932,816 B2 | 8/2005 | Phan |
| 6,934,134 B2 | 8/2005 | Mori et al. |
| 6,936,061 B2 | 8/2005 | Sasaki |
| D509,297 S | 9/2005 | Wells |
| 6,943,311 B2 | 9/2005 | Miyako |
| 6,953,430 B2 | 10/2005 | Kodooka |
| 6,953,461 B2 * | 10/2005 | McClurken et al. ........... 606/51 |
| 6,958,070 B2 | 10/2005 | Witt et al. |
| 6,960,210 B2 | 11/2005 | Lands et al. |
| 6,964,662 B2 | 11/2005 | Kidooka |
| 6,966,907 B2 | 11/2005 | Goble |

| | | | |
|---|---|---|---|
| 6,972,017 B2 | 12/2005 | Smith et al. | |
| 6,977,495 B2 | 12/2005 | Donofrio | |
| 6,979,786 B2 | 12/2005 | Aukland et al. | |
| 6,981,628 B2 | 1/2006 | Wales | |
| 6,987,244 B2 | 1/2006 | Bauer | |
| 6,994,707 B2 | 2/2006 | Ellman et al. | |
| 6,994,709 B2 | 2/2006 | Iida | |
| 6,997,931 B2 | 2/2006 | Sauer et al. | |
| 7,001,381 B2 | 2/2006 | Harano et al. | |
| 7,011,657 B2 | 3/2006 | Truckai et al. | |
| 7,033,354 B2 | 4/2006 | Keppel | |
| 7,033,356 B2 | 4/2006 | Latterell et al. | |
| 7,041,102 B2 | 5/2006 | Truckai et al. | |
| 7,044,948 B2 | 5/2006 | Keppel | |
| 7,052,489 B2 | 5/2006 | Griego et al. | |
| 7,052,496 B2 | 5/2006 | Yamauchi | |
| 7,063,715 B2 | 6/2006 | Onuki et al. | |
| D525,361 S | 7/2006 | Hushka | |
| 7,070,597 B2 | 7/2006 | Truckai et al. | |
| 7,083,618 B2 | 8/2006 | Couture et al. | |
| 7,083,619 B2 | 8/2006 | Truckai et al. | |
| 7,083,620 B2 | 8/2006 | Jahns et al. | |
| 7,087,051 B2 | 8/2006 | Bourne et al. | |
| 7,087,054 B2 | 8/2006 | Truckai et al. | |
| 7,090,673 B2 | 8/2006 | Dycus et al. | |
| 7,090,689 B2 | 8/2006 | Nagase et al. | |
| 7,101,371 B2 * | 9/2006 | Dycus et al. | 606/49 |
| 7,101,372 B2 | 9/2006 | Dycus et al. | |
| 7,101,373 B2 | 9/2006 | Dycus et al. | |
| 7,103,947 B2 | 9/2006 | Sartor et al. | |
| 7,107,124 B2 | 9/2006 | Green | |
| 7,112,199 B2 | 9/2006 | Cosmescu | |
| D531,311 S | 10/2006 | Guerra et al. | |
| 7,115,123 B2 | 10/2006 | Knowlton et al. | |
| 7,118,570 B2 | 10/2006 | Tetzlaff et al. | |
| 7,118,587 B2 | 10/2006 | Dycus et al. | |
| 7,131,860 B2 | 11/2006 | Sartor et al. | |
| 7,131,970 B2 | 11/2006 | Moses et al. | |
| 7,131,971 B2 | 11/2006 | Dycus et al. | |
| 7,135,020 B2 | 11/2006 | Lawes et al. | |
| D533,942 S | 12/2006 | Kerr et al. | |
| 7,145,757 B2 | 12/2006 | Shea et al. | |
| 7,147,638 B2 | 12/2006 | Chapman et al. | |
| 7,150,097 B2 | 12/2006 | Sremcich et al. | |
| 7,150,749 B2 | 12/2006 | Dycus et al. | |
| 7,153,314 B2 | 12/2006 | Laufer et al. | |
| D535,027 S | 1/2007 | James et al. | |
| 7,156,842 B2 | 1/2007 | Sartor et al. | |
| 7,156,846 B2 | 1/2007 | Dycus et al. | |
| 7,160,298 B2 | 1/2007 | Lawes et al. | |
| 7,160,299 B2 | 1/2007 | Baily | |
| 7,169,146 B2 | 1/2007 | Truckai et al. | |
| 7,179,255 B2 | 2/2007 | Lettice et al. | |
| 7,179,258 B2 | 2/2007 | Buysse et al. | |
| 7,195,631 B2 | 3/2007 | Dumbauld | |
| D541,418 S | 4/2007 | Schechter et al. | |
| 7,207,990 B2 | 4/2007 | Lands et al. | |
| D541,938 S | 5/2007 | Kerr et al | |
| 7,223,264 B2 | 5/2007 | Daniel et al. | |
| 7,223,265 B2 | 5/2007 | Keppel | |
| 7,232,440 B2 | 6/2007 | Dumbauld et al. | |
| 7,241,288 B2 | 7/2007 | Braun | |
| 7,241,296 B2 | 7/2007 | Buysse et al. | |
| 7,244,257 B2 | 7/2007 | Podjahsky et al. | |
| 7,246,734 B2 | 7/2007 | Shelton, IV | |
| 7,248,944 B2 | 7/2007 | Green | |
| 7,252,667 B2 | 8/2007 | Moses et al. | |
| 7,255,697 B2 | 8/2007 | Dycus et al. | |
| 7,267,677 B2 | 9/2007 | Johnson et al. | |
| 7,270,660 B2 | 9/2007 | Ryan | |
| 7,270,664 B2 | 9/2007 | Johnson et al. | |
| 7,276,068 B2 | 10/2007 | Johnson et al. | |
| 7,300,435 B2 | 11/2007 | Wham et al. | |
| 7,303,557 B2 | 12/2007 | Wham et al. | |
| 7,311,709 B2 | 12/2007 | Truckai et al. | |
| 7,314,471 B2 | 1/2008 | Holman | |
| 7,318,823 B2 | 1/2008 | Sharps et al. | |
| 7,329,256 B2 | 2/2008 | Johnson et al. | |
| 7,329,257 B2 | 2/2008 | Kanehira et al. | |
| D564,662 S | 3/2008 | Moses et al. | |
| 7,338,526 B2 | 3/2008 | Steinberg | |
| 7,342,754 B2 | 3/2008 | Fitzgerald et al. | |
| 7,344,268 B2 | 3/2008 | Jigamian | |
| D567,943 S | 4/2008 | Moses et al. | |
| 7,367,976 B2 | 5/2008 | Lawes et al. | |
| 7,377,920 B2 | 5/2008 | Buysse et al. | |
| 7,384,420 B2 | 6/2008 | Dycus et al. | |
| 7,384,421 B2 | 6/2008 | Hushka | |
| 7,396,336 B2 | 7/2008 | Orszulak et al. | |
| D575,395 S | 8/2008 | Hushka | |
| D575,401 S | 8/2008 | Hixson et al. | |
| 7,435,249 B2 | 10/2008 | Buysse et al. | |
| 7,442,193 B2 | 10/2008 | Shields et al. | |
| 7,442,194 B2 | 10/2008 | Dumbauld et al. | |
| 7,445,621 B2 | 11/2008 | Dumbauld et al. | |
| 7,458,972 B2 | 12/2008 | Keppel | |
| 7,473,253 B2 | 1/2009 | Dycus et al. | |
| 7,481,810 B2 | 1/2009 | Dumbauld et al. | |
| 7,487,780 B2 | 2/2009 | Hooven | |
| 7,491,201 B2 | 2/2009 | Shields et al. | |
| 7,491,202 B2 | 2/2009 | Odom et al. | |
| 7,500,975 B2 | 3/2009 | Cunningham et al. | |
| 7,510,556 B2 | 3/2009 | Nguyen et al. | |
| 7,513,898 B2 | 4/2009 | Johnson et al. | |
| 7,540,872 B2 | 6/2009 | Schechter et al. | |
| 7,549,995 B2 | 6/2009 | Schultz | |
| 7,553,312 B2 | 6/2009 | Tetzlaff et al. | |
| 2002/0049442 A1 | 4/2002 | Roberts et al. | |
| 2002/0107517 A1 | 8/2002 | Witt et al. | |
| 2002/0188294 A1 | 12/2002 | Couture et al. | |
| 2003/0014052 A1 | 1/2003 | Buysse et al. | |
| 2003/0014053 A1 | 1/2003 | Nguyen et al. | |
| 2003/0018331 A1 * | 1/2003 | Dycus et al. | 606/48 |
| 2003/0018332 A1 | 1/2003 | Schmaltz et al. | |
| 2003/0032956 A1 | 2/2003 | Lands et al. | |
| 2003/0069570 A1 | 4/2003 | Witzel et al. | |
| 2003/0069571 A1 | 4/2003 | Treat et al. | |
| 2003/0078578 A1 | 4/2003 | Truckai et al. | |
| 2003/0109875 A1 | 6/2003 | Tetzlaff et al. | |
| 2003/0114851 A1 | 6/2003 | Truckai et al. | |
| 2003/0139741 A1 | 7/2003 | Goble et al. | |
| 2003/0139742 A1 | 7/2003 | Wampler et al. | |
| 2003/0158548 A1 | 8/2003 | Phan et al. | |
| 2003/0158549 A1 | 8/2003 | Swanson | |
| 2003/0171747 A1 | 9/2003 | Kanehira et al. | |
| 2003/0181910 A1 | 9/2003 | Dycus et al. | |
| 2003/0216732 A1 | 11/2003 | Truckai et al. | |
| 2003/0229344 A1 | 12/2003 | Dycus et al. | |
| 2003/0236518 A1 | 12/2003 | Marchitto et al. | |
| 2004/0030330 A1 | 2/2004 | Brassell et al. | |
| 2004/0030332 A1 | 2/2004 | Knowlton et al. | |
| 2004/0064151 A1 | 4/2004 | Mollenauer | |
| 2004/0073238 A1 | 4/2004 | Makower | |
| 2004/0073256 A1 | 4/2004 | Marchitto et al. | |
| 2004/0078035 A1 | 4/2004 | Kanehira et al. | |
| 2004/0082952 A1 | 4/2004 | Dycus et al. | |
| 2004/0087943 A1 | 5/2004 | Dycus et al. | |
| 2004/0115296 A1 | 6/2004 | Duffin | |
| 2004/0116924 A1 | 6/2004 | Dycus et al. | |
| 2004/0122423 A1 | 6/2004 | Dycus et al. | |
| 2004/0138657 A1 * | 7/2004 | Bourne et al. | 606/41 |
| 2004/0143263 A1 | 7/2004 | Schechter et al. | |
| 2004/0147925 A1 | 7/2004 | Buysse et al. | |
| 2004/0148035 A1 | 7/2004 | Barrett et al. | |
| 2004/0162557 A1 | 8/2004 | Tetzlaff et al. | |
| 2004/0176762 A1 | 9/2004 | Lawes et al. | |

| | | | | | |
|---|---|---|---|---|---|
| 2004/0193153 A1 | 9/2004 | Sarter et al. | 2007/0078456 A1 | 4/2007 | Dumbauld et al. |
| 2004/0199181 A1 | 10/2004 | Knodel et al. | 2007/0078458 A1 | 4/2007 | Dumbauld et al. |
| 2004/0210282 A1 | 10/2004 | Flock et al. | 2007/0078459 A1 | 4/2007 | Johnson et al. |
| 2004/0224590 A1 | 11/2004 | Rawa et al. | 2007/0088356 A1 | 4/2007 | Moses et al. |
| 2004/0225288 A1 | 11/2004 | Buysse et al. | 2007/0106295 A1 | 5/2007 | Garrison et al. |
| 2004/0236325 A1 | 11/2004 | Tetzlaff et al. | 2007/0106297 A1 | 5/2007 | Dumbauld et al. |
| 2004/0236326 A1 | 11/2004 | Schulze et al. | 2007/0118111 A1 | 5/2007 | Weinberg |
| 2004/0243125 A1 | 12/2004 | Dycus et al. | 2007/0118115 A1 | 5/2007 | Artale et al. |
| 2004/0249371 A1 | 12/2004 | Dycus et al. | 2007/0142833 A1 | 6/2007 | Dycus et al. |
| 2004/0249374 A1 | 12/2004 | Tetzlaff et al. | 2007/0142834 A1 | 6/2007 | Dumbauld |
| 2004/0250419 A1 | 12/2004 | Sremcich et al. | 2007/0156139 A1 | 7/2007 | Schechter et al. |
| 2004/0254573 A1 | 12/2004 | Dycus et al. | 2007/0156140 A1 | 7/2007 | Baily |
| 2004/0260281 A1 | 12/2004 | Baxter, III et al. | 2007/0173811 A1 | 7/2007 | Couture et al. |
| 2005/0004568 A1 | 1/2005 | Lawes et al. | 2007/0173814 A1 | 7/2007 | Hixson et al. |
| 2005/0004569 A1 | 1/2005 | Witt et al. | 2007/0179499 A1 | 8/2007 | Garrison |
| 2005/0004570 A1 | 1/2005 | Chapman et al. | 2007/0198011 A1 | 8/2007 | Sugita |
| 2005/0021025 A1 | 1/2005 | Buysse et al. | 2007/0203485 A1 | 8/2007 | Keppel |
| 2005/0021026 A1 | 1/2005 | Baily | 2007/0213706 A1 | 9/2007 | Dumbauld et al. |
| 2005/0021027 A1 | 1/2005 | Shields et al. | 2007/0213707 A1 | 9/2007 | Dumbauld et al. |
| 2005/0059934 A1 | 3/2005 | Wenchell et al. | 2007/0213708 A1 | 9/2007 | Dumbauld et al. |
| 2005/0096645 A1 | 5/2005 | Wellman et al. | 2007/0213712 A1 | 9/2007 | Buysse et al. |
| 2005/0101951 A1 | 5/2005 | Wham et al. | 2007/0255279 A1 | 11/2007 | Buysse et al. |
| 2005/0101952 A1 | 5/2005 | Lands et al. | 2007/0260235 A1 | 11/2007 | Podhajsky |
| 2005/0107784 A1 | 5/2005 | Moses et al. | 2007/0260238 A1 | 11/2007 | Guerra |
| 2005/0107785 A1 | 5/2005 | Dycus et al. | 2007/0260241 A1 | 11/2007 | Dalla Betta et al. |
| 2005/0113818 A1 | 5/2005 | Sartor et al. | 2007/0260242 A1 | 11/2007 | Dycus et al. |
| 2005/0113826 A1 | 5/2005 | Johnson et al. | 2007/0265616 A1 | 11/2007 | Couture et al. |
| 2005/0113827 A1 | 5/2005 | Dumbauld et al. | 2008/0004616 A1 | 1/2008 | Patrick |
| 2005/0113828 A1 | 5/2005 | Shields et al. | 2008/0009860 A1 | 1/2008 | Odom |
| 2005/0119655 A1 | 6/2005 | Moses et al. | 2008/0015575 A1 | 1/2008 | Odom et al. |
| 2005/0149017 A1 | 7/2005 | Dycus | 2008/0021450 A1 | 1/2008 | Couture |
| 2005/0154387 A1 | 7/2005 | Moses et al. | 2008/0033428 A1 | 2/2008 | Artale et al. |
| 2005/0187547 A1 | 8/2005 | Sugi | 2008/0039835 A1 | 2/2008 | Johnson et al. |
| 2005/0197659 A1 | 9/2005 | Bahney | 2008/0039836 A1 | 2/2008 | Odom et al. |
| 2005/0203504 A1 | 9/2005 | Wham et al. | 2008/0045947 A1 | 2/2008 | Johnson et al. |
| 2005/0240179 A1 | 10/2005 | Buysse et al. | 2008/0058802 A1 | 3/2008 | Couture et al. |
| 2006/0052778 A1 | 3/2006 | Chapman et al. | 2008/0082100 A1 | 4/2008 | Orton et al. |
| 2006/0052779 A1 | 3/2006 | Hammill | 2008/0091189 A1 | 4/2008 | Carlton |
| 2006/0064085 A1 | 3/2006 | Schechter et al. | 2008/0114356 A1 | 5/2008 | Johnson et al. |
| 2006/0064086 A1 | 3/2006 | Odom | 2008/0167651 A1 | 7/2008 | Tetzlaff et al. |
| 2006/0074417 A1 | 4/2006 | Cunningham et al. | 2008/0195093 A1 | 8/2008 | Couture et al. |
| 2006/0079888 A1 | 4/2006 | Mulier et al. | 2008/0215051 A1 | 9/2008 | Buysse et al. |
| 2006/0079890 A1 | 4/2006 | Guerra | 2008/0243120 A1 | 10/2008 | Lawes et al. |
| 2006/0079933 A1 | 4/2006 | Hushka et al. | 2008/0249527 A1 | 10/2008 | Couture |
| 2006/0084973 A1 | 4/2006 | Hushka | 2008/0312653 A1 | 12/2008 | Arts et al. |
| 2006/0089670 A1 | 4/2006 | Hushka | 2008/0319442 A1 | 12/2008 | Unger et al. |
| 2006/0116675 A1 | 6/2006 | McClurken et al. | 2009/0012520 A1 | 1/2009 | Hixson et al. |
| 2006/0129146 A1 | 6/2006 | Dycus et al. | 2009/0018535 A1 | 1/2009 | Schechter et al. |
| 2006/0161150 A1 | 7/2006 | Keppel | 2009/0024126 A1 | 1/2009 | Artale et al. |
| 2006/0167450 A1 | 7/2006 | Johnson et al. | 2009/0043304 A1 | 2/2009 | Tetzlaff et al. |
| 2006/0167452 A1 | 7/2006 | Moses et al. | 2009/0048596 A1 | 2/2009 | Shields et al. |
| 2006/0173452 A1 | 8/2006 | Buysse et al. | 2009/0062794 A1 | 3/2009 | Buysse et al. |
| 2006/0189980 A1 | 8/2006 | Johnson et al. | 2009/0082766 A1 | 3/2009 | Unger et al. |
| 2006/0189981 A1 | 8/2006 | Dycus et al. | 2009/0082767 A1 | 3/2009 | Unger et al. |
| 2006/0190035 A1 | 8/2006 | Hushka et al. | 2009/0082769 A1 | 3/2009 | Unger et al. |
| 2006/0217709 A1 | 9/2006 | Couture et al. | 2009/0088738 A1 | 4/2009 | Guerra et al. |
| 2006/0224158 A1 | 10/2006 | Odom et al. | 2009/0088739 A1 | 4/2009 | Hushka et al. |
| 2006/0229666 A1 | 10/2006 | Suzuki et al. | 2009/0088740 A1 | 4/2009 | Guerra et al. |
| 2006/0253126 A1 | 11/2006 | Bjerken et al. | 2009/0088741 A1 | 4/2009 | Hushka et al. |
| 2006/0259036 A1 | 11/2006 | Tetzlaf et al. | 2009/0088744 A1 | 4/2009 | Townsend |
| 2006/0264922 A1 | 11/2006 | Sartor et al. | 2009/0088745 A1 | 4/2009 | Hushka et al. |
| 2006/0264931 A1 | 11/2006 | Chapman et al. | 2009/0088746 A1 | 4/2009 | Hushka et al. |
| 2006/0271038 A1 | 11/2006 | Johnson et al. | 2009/0088747 A1 | 4/2009 | Hushka et al. |
| 2006/0283093 A1 | 12/2006 | Petrovic et al. | 2009/0088748 A1 | 4/2009 | Guerra et al. |
| 2006/0287641 A1 | 12/2006 | Perlin | 2009/0088749 A1 | 4/2009 | Hushka et al. |
| 2007/0016182 A1 | 1/2007 | Lipson et al. | 2009/0088750 A1 | 4/2009 | Hushka et al. |
| 2007/0016187 A1 | 1/2007 | Weinberg et al. | 2009/0112206 A1 | 4/2009 | Dumbauld et al. |
| 2007/0043352 A1 | 2/2007 | Garrison et al. | 2009/0131934 A1 | 5/2009 | Odom et al. |
| 2007/0043353 A1 | 2/2007 | Dycus et al. | 2009/0149853 A1 | 6/2009 | Shields et al. |
| 2007/0055231 A1 | 3/2007 | Dycus et al. | 2009/0149854 A1 | 6/2009 | Cunningham et al. |
| 2007/0060919 A1 | 3/2007 | Isaacson et al. | 2009/0171350 A1 | 7/2009 | Dycus et al. |
| 2007/0062017 A1 | 3/2007 | Dycus et al. | 2009/0171353 A1 | 7/2009 | Johnson et al. |
| 2007/0074807 A1 | 4/2007 | Guerra | 2009/0182327 A1 | 7/2009 | Unger |

| | | | |
|---|---|---|---|
| 2009/0187188 A1 | 7/2009 | Guerra et al. | |

FOREIGN PATENT DOCUMENTS

| | | |
|---|---|---|
| DE | 2415263 | 10/1975 |
| DE | 2514501 | 10/1976 |
| DE | 2627679 | 1/1977 |
| DE | 3612646 | 4/1987 |
| DE | 4303882 | 8/1994 |
| DE | 4403252 | 8/1995 |
| DE | 19515914 | 7/1996 |
| DE | 29616210 | 1/1997 |
| DE | 19608716 | 4/1997 |
| DE | 19751106 | 5/1998 |
| DE | 19751108 | 5/1999 |
| DE | 19738457 | 1/2009 |
| EP | 0364216 A1 | 4/1990 |
| EP | 0467501 | 1/1992 |
| EP | 518230 A1 | 12/1992 |
| EP | 0 541 930 B1 | 5/1993 |
| EP | 0572131 | 12/1993 |
| EP | 584787 A1 | 3/1994 |
| EP | 0589453 A2 | 3/1994 |
| EP | 0589555 | 3/1994 |
| EP | 0623316 A1 | 11/1994 |
| EP | 0624348 A2 | 11/1994 |
| EP | 0650701 A1 | 5/1995 |
| EP | 0694290 A3 | 3/1996 |
| EP | 0717966 A1 | 6/1996 |
| EP | 0754437 A3 | 3/1997 |
| EP | 0517243 | 9/1997 |
| EP | 853922 A1 | 7/1998 |
| EP | 0887046 A3 | 1/1999 |
| EP | 0923907 A1 | 6/1999 |
| EP | 1034747 A1 | 9/2000 |
| EP | 1034748 A1 | 9/2000 |
| EP | 1025807 A3 | 10/2000 |
| EP | 1034746 A3 | 10/2000 |
| EP | 1050278 A1 | 11/2000 |
| EP | 1053719 A1 | 11/2000 |
| EP | 1053720 A1 | 11/2000 |
| EP | 1055399 A1 | 11/2000 |
| EP | 1055400 A1 | 11/2000 |
| EP | 1080694 A1 | 3/2001 |
| EP | 1082944 A1 | 3/2001 |
| EP | 1159926 A2 | 12/2001 |
| EP | 1177771 | 2/2002 |
| EP | 1301135 A | 4/2003 |
| EP | 1472984 A1 | 11/2004 |
| EP | 0774232 | 1/2005 |
| EP | 1527747 A2 | 5/2005 |
| EP | 1530952 A1 | 5/2005 |
| EP | 1535581 A2 | 6/2005 |
| EP | 1609430 A1 | 12/2005 |
| EP | 1632192 A1 | 3/2006 |
| EP | 1642543 | 4/2006 |
| EP | 1645238 A1 | 4/2006 |
| EP | 1645240 A2 | 4/2006 |
| EP | 1649821 | 4/2006 |
| EP | 1707143 A1 | 10/2006 |
| EP | 1769765 | 4/2007 |
| EP | 1769766 | 4/2007 |
| EP | 1929970 | 6/2008 |
| EP | 1683496 | 12/2008 |
| GB | 623316 | 5/1949 |
| GB | 1490585 | 11/1977 |
| GB | 2214430 A | 6/1989 |
| GB | 2213416 | 8/1989 |
| JP | 501068 | 9/1984 |
| JP | 502328 | 3/1992 |
| JP | 5-5106 | 1/1993 |
| JP | 5-40112 | 2/1993 |
| JP | 06343644 A2 | 12/1994 |
| JP | 07265328 A2 | 10/1995 |
| JP | 08056955 A2 | 3/1996 |
| JP | 08252263 A2 | 10/1996 |
| JP | 09010223 A2 | 1/1997 |
| JP | 11244298 A2 | 9/1999 |
| JP | 2000342599 A2 | 12/2000 |
| JP | 2000350732 A2 | 12/2000 |
| JP | 2001008944 A2 | 1/2001 |
| JP | 2001029356 A2 | 2/2001 |
| JP | 2001128990 A2 | 5/2001 |
| RU | 401367 | 10/1973 |
| SU | 401367 | 11/1974 |
| WO | WO89/00757 | 1/1989 |
| WO | WO 92/04873 | 4/1992 |
| WO | WO 92/06642 | 4/1992 |
| WO | WO 93/21845 | 11/1993 |
| WO | WO 94/08524 A | 4/1994 |
| WO | WO94/20025 | 9/1994 |
| WO | WO 95/02369 | 1/1995 |
| WO | WO95/07662 | 3/1995 |
| WO | WO 95/07662 | 3/1995 |
| WO | WO95/15124 | 6/1995 |
| WO | WO96/05776 | 2/1996 |
| WO | WO 96/13218 | 9/1996 |
| WO | WO 97/00646 | 1/1997 |
| WO | WO 97/00647 | 1/1997 |
| WO | WO97/10764 | 3/1997 |
| WO | WO 97/10764 | 3/1997 |
| WO | WO 97/24073 | 7/1997 |
| WO | WO 97/24993 | 7/1997 |
| WO | WO 98/27880 | 7/1998 |
| WO | WO 99/03407 | 1/1999 |
| WO | WO 99/03408 | 1/1999 |
| WO | WO 99/03409 | 1/1999 |
| WO | WO 99/12488 | 3/1999 |
| WO | WO 99/23933 | 5/1999 |
| WO | WO 99/40857 | 8/1999 |
| WO | WO 99/51158 | 10/1999 |
| WO | WO 99/66850 A | 12/1999 |
| WO | WO 00/24330 | 5/2000 |
| WO | WO 00/24331 | 5/2000 |
| WO | WO00/24331 | 5/2000 |
| WO | WO 00/36986 | 6/2000 |
| WO | WO 00/41638 | 7/2000 |
| WO | WO00/47124 | 8/2000 |
| WO | WO 00/53112 | 9/2000 |
| WO | WO 01/17448 A | 3/2001 |
| WO | WO 01/54604 | 8/2001 |
| WO | WO02/07627 | 1/2002 |
| WO | WO 02/07627 | 1/2002 |
| WO | WO 02/067798 A1 | 9/2002 |
| WO | WO02/080783 | 10/2002 |
| WO | WO 02/080783 | 10/2002 |
| WO | WO02/080784 | 10/2002 |
| WO | WO 02/080784 | 10/2002 |
| WO | WO 02/080785 | 10/2002 |
| WO | WO02/080785 | 10/2002 |
| WO | WO 02/080786 | 10/2002 |
| WO | WO02/080786 | 10/2002 |
| WO | WO 02/080793 | 10/2002 |
| WO | WO02/080793 | 10/2002 |
| WO | WO 02/080794 | 10/2002 |
| WO | WO02/080794 | 10/2002 |
| WO | WO 02/080795 | 10/2002 |
| WO | WO 02/080796 | 10/2002 |
| WO | WO 02/080797 | 10/2002 |
| WO | WO02/080797 | 10/2002 |
| WO | WO 02/080798 | 10/2002 |
| WO | WO 02/080799 | 10/2002 |
| WO | WO 02/081170 | 10/2002 |
| WO | WO02/081170 | 10/2002 |
| WO | WO 03/061500 | 7/2003 |
| WO | WO 03/090630 A3 | 11/2003 |

| | | |
|---|---|---|
| WO | WO 2004/032776 A1 | 4/2004 |
| WO | WO2004/032777 | 4/2004 |
| WO | WO 2004/032777 | 4/2004 |
| WO | WO 2004/052221 | 6/2004 |
| WO | WO 2004/073488 A2 | 9/2004 |
| WO | WO 2004/073490 | 9/2004 |
| WO | WO2004/073490 | 9/2004 |
| WO | WO2004/073753 | 9/2004 |
| WO | WO 2004/082495 | 9/2004 |
| WO | WO 2004/098383 | 11/2004 |
| WO | WO 2004/103156 | 12/2004 |
| WO | WO 2005/004734 A1 | 1/2005 |
| WO | WO2005/004735 | 1/2005 |
| WO | WO 2005/110264 | 11/2005 |
| WO | WO 2008/045348 | 4/2008 |
| WO | WO 2008/045350 | 4/2008 |

OTHER PUBLICATIONS

Bergdahl et al. "Studies on Coagulation and the Development of an Automatic Computerized Bipolar Coagulator" J.Neurosurg, vol. 75, Jul. 1991, pp. 148-151.
Kennedy et al. "High-burst-strength, feedback-controlled bipolar vessel sealing" Surgical Endoscopy (1998) 12:876-878.
Peterson et al. "Comparison of Healing Process Following Ligation with Sutures and Bipolar Vessel Sealing" Surgical Technology International (2001).
Linehan et al. "A Phase I Study of the LigaSure Vessel Sealing System in Hepatic Surgery" Section of HPB Surger, Washington University School of Medicine, St, Louis MO, Presented at AHPBA, Feb. 2001.
Johnson et al. "Evaluation of the LigaSure Vessel Sealing System in Hemorrhoidectormy" American College of Surgeons (ACS) Clinicla Congress Poster (2000).
Sayfan et al. "Sutureless Closed Hemorrhoidectomy: A New Technique" Annals of Surgery vol. 234 No. 1 Jul. 2001 pp. 21-24.
Heniford et al. "Initial Results with an Electrotherrnal Bipolar Vessel Sealer" Surgical Endoscopy (2000) 15:799-801.
Heniford et al. "Initial Research and Clinical Results with an Electrothermal Bipolar Vessel Sealer" Oct. 1999.
McLellan at al. "Vessel Sealing for Hemostasis During Pelvic Surgery" Int'l Federation of Gynecology and Obstetrics Figo World Congress 2000, Washington, D.C.
Levy et al. "Use of a New Energy-based Vessel Ligation Device During Vaginal Hysterectomy" Int'l Federation of Gynecology and Obstetrics (Figo) World Congress.
Crawford et al. "Use of the LigaSure Vessel Sealing System in Urologic Cancer Surger" Grand Rounds in Urology 1999 vol. 1 Issue 4 pp. 10-17.
Rothenberg et al. "Use of the LigaSure Vessel Sealing System in Minimally Invasive Surgery in Children" Int'l Pediatric Endosurgery Group (IPEG) 2000.
Palazzo et al. "Randomized clinical trial of Ligasure versus open haemorrhoidectomy" British Journal of Surgery 2002, 89, 154-157.
"Innovations in Electrosurgery" Sales/Product Literature; Dec. 31, 2000.
LigaSure Vessel Sealing System, the Seal of Confidence in General, Gynecologic, Urologic, and Laparaoscopic Surgery Sales/Product Literature; Jan. 2004.
Carbonell et al., "Comparison of theGyrus PlasmaKinetic Sealer and the Valleylab LigaSure Device in the Hemostasis of Small, Medium, and Large-Sized Arteries" Carolinas Laparoscopic and Advanced Surgery Program, Carolinas Medical Center, Charlotte, NC.
"Reducing Needlestick Injuries in the Operating Room" Sales/Product Literature.
Chung et al., "Clinical Experience of Sutureless Closed Hemorrhoidectomy with LigaSure" Diseases of the Colon & Rectum vol. 46, No. 1 Jan. 2003.
Strasberg at al., "Use of a Bipolar Vessel-Sealing Device for Parenchymal Transection During Liver Surgery" Journal of Gastrointestinal Surgery, vol. 6, No. 4, Jul./Aug. 2002 pp. 569-574.
Paul G. Horgan, "A Novel Technique for Parenchymal Division During Hepatectomy" The American Journal of Surgery, vol. 181, No. 3, Apr. 2001 pp. 236-237.
W. Scott Helton, "LigaSure Vessel Sealing System: Revolutionary Hemostasis Product for General Surgery" Sales/Product Literature.
Michael Choti, "Abdominoperineal Resection with the LigaSure Vessel Sealing System and LigaSure Atlas 20 cm Open Instrument" Innovations That Work, Jun. 2003.
Craig Johnson, "Use of the LigaSure Vessel Sealing System in Bloodless Hemorrhoidectomy" Innovations That Work, Mar. 2000.
Muller et al., "Extended Left Hemicolectomy Using the LigaSure Vessel Sealing System" Inovations That Work, Sep. 1999.
Herman at al., "Laparoscopic Intestinal Resection Wth the LigaSure Vessel Sealing System: A Case Report" Innovations That Work, Feb. 2002.
Carus at al., "Initial Experience With The LigaSure Vessel Sealing System in Abdominal Surgery" Innovations That Work, Jun. 2002.
Levy et al. "Randomized Trial of Suture Versus Electrosurgical Bipolar Vessel Sealing in Vaginal Hysterectomy" Obstetrics & Gynecology, vol. 102, No. 1, Jul. 2003.
Levy et al., "Update on Hysterectomy—New Technologies and Techniques" OBG Management, Feb. 2003.
Barbara Levy, "Use of a New Vessel Ligation Device During Vaginal Hysterectomy" FIGO 2000, Washington, D.C.
McLellan et al. "Vessel Sealing For Hemostasis During Gynecologic Surgery" Sales/Products Literature.
Sengupta et al., "Use of a Computer-Controlled Bipolar Diathermy System in Radical Prostatectomies and Other Open Urological Surgery" ANZ Journal of Surgery (2001) 71.9 pp. 538-540.
Olsson et al. "Radical Cystectomy in Females" Current Surgical Techniques in Urology, vol. 14, Issue 3, 2001.
E. David Crawford "Use of a Novel Vessel Sealing Technology in Management of the Dorsal Veinous Complex" Sales/Product Literature.
Jarrett et al., "Use of the LigaSure Vessel Sealing System for Peri-Hilar Vessels in Laparoscopic Nephrectomy" Sales/Product Literature.
E. David Crawford "Evaluation of a New Vessel Sealing Device in Urologic Cancer Surgery" Sales/Product Literature.
Joseph Ortenberg "LigaSure System Used in Laparoscopic 1st and 2nd Stage Orchiopexy" Innovations That Work, Nov. 2002.
Koyle et al., "Laparoscopic Palomo Varicocele Ligation in Children and Adolescents" Pediatric Endosurgery & Innovative Techniques, vol. 6, No. 1, 2002.
Dulemba et al. "Use of a Bipolar Electrothermal Vessel Sealer in Laparoscopically Assisted Vaginal Hysterectomy" Sales/Product Literature; Jan. 2004.
Johnson et al. "Evaluation of a Bipolar electrothermal Vessel Sealing Device in Hemorrhoidectomy" Sales/Product Literature; Jan. 2004.
Int'l Search Report PCT/US98/18640.
Int'l Search Report PCT/US98/23950.
Int'l Search Report PCT/US99/24869.
Int'l Search Report PCT/US01/11218.
Int'l Search Report PCT/US01/11340.
Int'l Search Report PCT/US01/11420.
Int'l Search Report PCT/US02/01890.
Int'l Search Report PCT/US02/11100.
Int'l Search Report PCT/US04/03436.
Int'l Search Report PCT/US04/13273.
Int'l Search Report PCT/US04/15311.
Int'l Search Report EP 98944778.
Int'l Search Report EP 98958575.
Int'l Search Report EP 04027314.
Int'l Search Report EP 04027479.
Int'l Search Report EP 04027705.
Int'l Search Report EP 04013772.
"Innovations in Electrosurgery" Sales/Product Literature; Dec. 31, 2000.
LigaSure Vessel Sealing System, the Seal of Confidence in General, Gynecologic, Urologic, and Laparaoscopic Surgery Sales/Product Literature; Jan. 2004.
Olsson et al. "Radical Cystectomy in Females" Current Surgical Techniques in Urology, vol. 14, Issue 3, 2001.

Dulemba et al. "Use of a Bipolar Electrothermal Vessel Sealer in Laparoscopically Assisted Vaginal Hysterectomy" Sales Product Literature; Jan. 2004.
Johnson et al. "Evaluation of a Bipolar electrothermal Vessel Sealing Device in Hemorrhoidectomy" Sales Product Literature; Jan. 2004.
Levy et al. "Use of a New Energy-based Vessel Ligation Device During Vaginal Hysterectomy" Int'l Federation of Gynecology and Obstetrics (FIGO) World Congress 1999.
Carbonell et al., "Comparison of the Gyrus PlasmaKinetic Sealer and the Valleylab LigaSure Device in the Hemostasis of Small, Medium, and Large-Sized Arteries" Carolinas Laparoscopic and Advanced Surgery Program, Carolinas Medical Center, Charlotte, NC 2003.
"Reducing Needlestick Injuries in the Operating Room" Sales/Product Literature 2001.
W. Scott Helton, "LigaSure Vessel Sealing System: Revolutionary Hemostasis Product for General Surgery" Sales/Product Literature 1999.
McLellan et al. "Vessel Sealing For Hemostasis During Gynecologic Surgery" Sales/Product Literature 1999.
E. David Crawford "Use of a Novel Vessel Sealing Technology in Management of the Dorsal Veinous Complex" Sales/Product Literature 2000.
Jarrett et al., "Use of the LigaSure Vessel Sealing System for Peri-Hilar Vessels in Laparoscopic Nephrectomy" Sales/Product Literature 2000.
E. David Crawford "Evaluation of a New Vessel Sealing Device in Urologic Cancer Surgery" Sales/Product Literature 2000.
International Search Report PCT/US01/11224 dated Nov. 13, 2001.
International Search Report EP 98958575.7 dated Sep. 20, 2002.
International Search Report EP 04013772 dated Apr. 1, 2005.
International Search Report EP 05013895 dated Oct. 14, 2005.
International Search Report EP 05017281 dated Nov. 16, 2005.
Int'l Search Report EP 05016399 dated Jan. 5, 2006.
Int'l Search Report EP 06005185.1 dated Apr. 18, 2006.
Int'l Search Report EP 06008779.8 dated Jun. 13, 2006.
Int'l Search Report EP 1683496 dated Jun. 13, 2006.
Int'l Search Report EP 04013772 dated Apr. 1, 2005.
Int'l Search Report EP 05013895 dated Oct. 14, 2005.
Int'l Search Report EP 05017281 dated Nov. 16, 2005.
Int'l Search Report EP 06006716 dated Aug. 4, 2006.
Int'l Search Report PCT/US01/11224 dated Nov. 13, 2001.
Int'l Search Report EP 06014461.5 dated Oct. 20, 2006.
Int'l Search Report EP 06020584.6 dated Jan. 12, 2007.
Int'l Search Report EP 06020583.8 dated Jan. 30, 2007.
Int'l Search Report EP 06020756.0 dated Feb. 5, 2007.
Int'l Search Report EP 06024123.9 dated Feb. 26, 2007.
Int'l Search Report EP 04 752343.6 dated Jul. 20, 2007.
Int'l Search Report EP 06 024122.1 dated Mar. 19, 2007.
Int'l Search Report EP 07 001480.8 dated Apr. 12, 2007.
Int'l Search Report EP 07 001488.1 dated May 29, 2007.
Int'l Search Report—Extended EP 07 009029.5 dated Jul. 12, 2007.
Int'l Search Report EP 07 009321.6 dated Aug. 17, 2007.
Int'l Search Report EP 05016399 dated Jan. 5, 2006.
Int'l Search Report EP 06005185.1 dated Apr. 18, 2006.
Int'l Search Report EP 06008779.8 dated Jun. 13, 2006.
Int'l Search Report EP 1683496 dated Jun. 13, 2006.
Int'l Search Report EP 06 020574.7 dated Sep. 21, 2007.
Int'l Search Report EP 07 010672.9 dated Oct. 1, 2007.
Int'l Search Report EP 07 013779.9 dated Oct. 18, 2007.
Int'l Search Report EP 07 009026.1 dated Sep. 12, 2007.
Int'l Search Report EP 07 015601.3 dated Dec. 6, 2007.
Int'l Search Report EP 07 015191.5 dated Dec. 19, 2007.
Int'l Search Report EP 07 020283.3 dated Jan. 16, 2008.
Sampayan et al, "Multilayer Ultra-High Gradient Insulator Technology" Discharges and Electrical Insulation in Vacuum, 1998. Netherlands Aug. 17-21, 1998; vol. 2, pp. 740-743.
Crouch et al. "A Velocity-Dependent Model for Needle Insertion in Soft Tissue" MICCAI 2005; LNCS 3750 pp. 624-632, Dated: 2005.
Int'l Search Report EP 98957771 dated Aug. 9, 2001.
Int'l Search Report EP 05002671.5 dated Dec. 22, 2008.
Int'l Search Report EP 05002674.9 dated Jan. 16, 2009.
Int'l Search Report EP 05019429.9 dated May 6, 2008.
Int'l Search Report EP 06008515.6 dated Jan. 8, 2009.
Int'l Search Report EP 07 014016 dated Jan. 28, 2008.
Int'l Search Report EP 07 021646.0 dated Jul. 9, 2008.
Int'l Search Report EP 07 021647.8 dated May 2, 2008.
Int'l Search Report EP 08 02692.5 dated Dec. 12, 2008.
Int'l Search Report EP 08 004655.0 dated Jun. 24, 2008.
Int'l Search Report EP 08 006732.5 dated Jul. 29, 2008.
Int'l Search Report EP 08 006917.2 dated Jul. 3, 2008.
Int'l Search Report EP 08 016539.2 dated Jan. 8, 2009.
Int'l Search Report EP 09 152267.2 Dated Jun. 15, 2009.
Int'l Search Report EP 09 152898.4 Dated Jun. 10, 2009.
Int'l Search Report PCT/US98/24281 dated Feb. 22, 1999.
Int'l Search Report PCT/US03/28534 dated Dec. 19, 2003.
Int'l Search Report PCT/US07/021438 dated Apr. 1, 2008.
Int'l Search Report PCT/US07/021440 dated Apr. 8, 2008.
Int'l Search Report PCT/US08/61498 dated Sep. 22, 2008.
Int'l Search Report PCT/US09/032690 dated Jun. 16, 2009.
Sampayan et al, "Multilayer Ultra-High Gradient Insulator Technology" Discharges and Electrical Insulation in Vacuum, 1998. Netherlands Aug. 17-21, 1998; vol. 2, pp. 740-743.
Crouch et al. "A Velocity-Dependent Model for Needle Insertion in Soft Tissue" MICCAI 2005; LNCS 3750 pp. 624-632, Dated: 2005.
Int'l Search Report EP 98957771 dated Aug. 9, 2001.
Int'l,Search Report EP 05002671.5 dated Dec. 22, 2008.
Int'l Search Report EP 05002674.9 dated Jan. 16, 2009.
Int'l Search Report EP 05019429.9 dated May 6, 2008.
Int'l Search Report EP 06008515.6 dated Jan. 8, 2009.
Int'l Search Report EP 07 014016 dated Jan. 28, 2008.
Int'l Search Report EP 07 021646.0 dated Jul. 9, 2008.
Int'l Search Report EP 07 021647.8 dated May 2, 2008.
Int'l Search Report EP 08 02692.5 dated Dec. 12, 2008.
Int'l Search Report EP 08 004655.0 dated Jun. 24, 2008.
Int'l Search Report EP 08 006732.5 dated Jul. 29, 2008.
Int'l Search Report EP 08 006917.2 dated Jul. 3, 2008.
Int'l Search Report EP 08 016539.2 dated Jan. 8, 2009.
Int'l Search Report EP 09 152267.2 Dated Jun. 15, 2009.
Int'l Search Report EP 09 152898.4 Dated Jun. 10, 2009.
Int'l Search Report PCT/US98/24281 dated Feb. 22, 1999.
Int'l Search Report PCT/US03/28534 dated Dec. 19, 2003.
Int'l Search Report PCT/US07/021438 dated Apr. 1, 2008.
Int'l Search Report PCT/US07/021440 dated Apr. 8, 2008.
Int'l Search Report PCT/US08/61498 dated Sep. 22, 2008.
Int'l Search Report PCT/US09/032690 dated Jun. 16, 2009.

* cited by examiner

INCORPORATING RAPID COOLING IN TISSUE FUSION HEATING PROCESSES

CROSS REFERENCE TO RELATED APPLICATIONS

The present application is a continuation-in-part (CIP) of PCT Application Serial No. PCT/US04/13273 filed on Apr. 29, 2004 entitled "ELECTROSURGICAL INSTRUMENT WHICH REDUCES THERMAL DAMAGE TO ADJACENT TISSUE" which claims the benefit of priority to U.S. Provisional Application Ser. No. 60/467,027 filed on May 1, 2003 by Chapman et al., the entire contents of both of which are incorporated by reference herein.

BACKGROUND

1. Technical Field

The present disclosure relates to electrosurgical instruments used for open and endoscopic surgical procedures for sealing or fusing tissue. More particularly, the present disclosure relates to a bipolar forceps for sealing vessels, vascular tissues and soft tissues having an electrode sealing assembly which is designed to limit and/or reduce by rapid cooling thermal spread to adjacent tissue structures.

2. Related Prior Art

Electrosurgical forceps utilize both mechanical clamping action and electrical energy to effect hemostasis by heating the tissue and blood vessels to coagulate and/or cauterize vessels or tissue. However, certain surgical procedures may require sealing blood vessels or vascular tissue rather than just simply effecting hemostasis. "Vessel sealing" or "Tissue Fusion" is defined as the process of liquefying the collagen, elastin and ground substances in the tissue so that it reforms into a fused mass with significantly-reduced demarcation between the opposing tissue structures. In contrast, the term "cauterization" is defined as the use of heat to destroy tissue (also called "diathermy" or "electrodiathermy") and the term "coagulation" is defined as a process of desiccating tissue wherein the tissue cells are ruptured and dried. Coagulation of small vessels is usually sufficient to permanently close them. Larger vessels or tissue need to be "sealed" to assure permanent closure.

Numerous electrosurgical instruments have been proposed in the past for various open and endoscopic surgical procedures. However, most of these instruments cauterize or coagulate tissue and are normally not designed to provide uniformly reproducible pressure on the blood vessel or tissue which, if used for sealing purposes, would result in an ineffective or non-uniform seal. For example, U.S. Pat. No. 2,176,479 to Willis, U.S. Pat. Nos. 4,005,714 and 4,031,898 to Hiltebrandt, U.S. Pat. Nos. 5,827,274, 5,290,287 and 5,312,433 to Boebel et al., U.S. Pat. Nos. 4,370,980, 4,552,143, 5,026,370 and 5,116,332 to Lottick, U.S. Pat. No. 5,443,463 to Stern et al., U.S. Pat. No. 5,484,436 to Eggers et al. and U.S. Pat. No. 5,951,549 to Richardson et al., all relate to electrosurgical instruments for coagulating, cauterizing, and cutting vessels or tissue.

Many of these instruments include blade members or shearing members which simply cut tissue in a mechanical and/or electromechanical manner and are relatively ineffective for vessel sealing purposes. Other instruments generally rely on clamping pressure alone to procure proper sealing thickness and are often not designed to take into account gap tolerances and/or parallelism and flatness requirements which are parameters which, if properly controlled, can assure a consistent and effective tissue seal. For example, it is known that it is difficult to adequately control thickness of the resulting sealed tissue by controlling clamping pressure alone for either of two reasons: 1) if too much force is applied, there is a possibility that the two poles will touch and energy will not be transferred through the tissue resulting in an ineffective seal; or 2) if too low a force is applied, a thicker less reliable seal is created.

Commonly-owned U.S. Application Serial Nos. PCT Application Serial No. PCT/US01/11340 filed on Apr. 6, 2001 by Dycus, et al. entitled "VESSEL SEALER AND DIVIDER", U.S. application Ser. No. 10/116,824 filed on Apr. 5, 2002 by Tetzlaff et al. entitled "VESSEL SEALING INSTRUMENT" and PCT Application Serial No. PCT/US01/11420 filed on Apr. 6, 2001 by Tetzlaff et al. entitled "VESSEL SEALING INSTRUMENT" teach that to effectively seal tissue or vessels, especially large vessels, two predominant mechanical parameters must be accurately controlled: 1) the pressure applied to the vessel; and 2) the gap distance between the conductive tissue contacting surfaces (electrodes). As can be appreciated, both of these parameters are affected by the thickness of the vessel or tissue being sealed. Accurate application of pressure is important for several reasons: to reduce the tissue impedance to a low enough value that allows enough electrosurgical energy through the tissue; to overcome the forces of expansion during tissue heating; and to contribute to the end tissue thickness which is an indication of a good seal.

It has been found that using electrosurgical instruments to seal tissue may result in some degree of so-called "thermal spread" across adjacent tissue structures. "Thermal spread" refers generally to the heat transfer traveling along the periphery of the electrically conductive surfaces. This can also be termed "collateral damage" to adjacent tissue. As can be appreciated, reducing the thermal spread during an electrical procedure reduces the likelihood of unintentional or undesirable collateral damage to surrounding tissue structures which are adjacent to an intended treatment site. Reducing the collateral damage to surrounding tissue or maintaining the viability of surrounding tissue after the sealing process is known to promote tissue healing and decrease overall healing time by stimulating/improving healing response. Controlling tissue cooling may also reduce adhesion or buildup of tissue on the electrodes and also assist during the formation of the tissue seal, e.g., cross-linking or other chemical bonding, during the reformation or renaturation of collagen.

Instruments which include dielectric coatings disposed on the outer surfaces are known and are used to prevent tissue "blanching" at points normal to the sealing site. In other words, these coatings are primarily designed to reduce accidental burning of tissue as a result of incidental contact with the outer surfaces of the end effectors. So far as is known, these coatings are not designed or intended to reduce collateral tissue damage or thermal spread to adjacent tissue (tissue lying along the tissue plane).

Commonly-owned U.S. patent Ser. No. 10/474,168 entitled "ELECTROSURGICAL INSTRUMENT WHICH REDUCES COLLATERAL DAMAGE TO ADJACENT TISSUE" filed on Oct. 3, 2003 by Buysse et al. relates to an instrument which is configured to control or regulate the electrical field around the electrically conductive sealing surfaces to reduce stray current concentrations which can result in thermal spread to adjacent tissue structures.

Thus, a need exists to develop an electrosurgical instrument which includes an electrode sealing assembly which can seal vessels and tissue consistently and effectively and reduce the undesirable effects of thermal spread across or to adjacent tissue structures by utilizing a thermally conductive, electrically non-conductive material.

In addition, in tissue fusion applications that utilize energy to treat tissue, the need exists to maximize and enhance tissue strength at the tissue fusion site and minimize detrimental tissue effects to adjacent or surrounding tissue structures.

SUMMARY

It is an object of the present disclosure to provide an electrode sealing assembly designed for use with an electrosurgical instrument for sealing tissue which rapidly cools during or after tissue fusion heating processes.

The present disclosure generally relates to an electrode sealing assembly for use with an electrosurgical instrument for sealing tissue. The electrode sealing assembly includes first and second jaw members which are movable from a first position in spaced relation relative to one another to at least one second position for grasping tissue therebetween. The jaw members include electrically conductive sealing plates disposed in opposing relation to one another. At least one jaw member includes a thermoelectric cooling plate having a first surface in direct contact with an outer surface of the sealing plate. The thermoelectric cooling plate include first and second electrical connections disposed on opposite sides of the thermoelectric cooling plate. The first connection is configured to selectively transmit a first electrical potential and the second connection is configured to selectively transmit a second electrical potential such that heat generated by the sealing plates is transferred away from the tissue via the thermoelectric cooling plate.

The heat sink may be configured to be coupled to an ultimate heat sink for transferring heat from the jaw member(s). The heat sink may include a coolant line disposed therethrough. The coolant line may be configured to receive a coolant to transfer heat from the thermoelectric cooling plate. In one embodiment, the coolant is a thermally conductive, non-electrically conductive fluid which may be one of the group consisting of air, nitrogen, carbon dioxide, and 3M™ Fluorinert™ Electronic Liquid FC-7 (available from 3M Company, St. Paul, Minn.).

In one particularly useful embodiment, the present disclosure relates to an electrode sealing assembly designed for use with an electrosurgical instrument for sealing tissue. The electrode sealing assembly includes first and second electrode jaw members which are movable from a first position in spaced relation relative to one another to at least one second position for grasping tissue therebetween. The jaw members include sealing plates disposed in opposing relation relative to one another. Each jaw member includes a cooling line disposed therethrough which is configured to convey a cooling liquid therethrough to absorb heat from the sealing plates during or after sealing.

The cooling line may be configured to be coupled to a second or an ultimate heat sink for transferring heat from the jaw member(s). In addition, the cooling line may be configured to receive a coolant to transfer heat from the jaw member (s). In one embodiment, the coolant is a thermally conductive, non-electrically conductive fluid.

In another particularly useful embodiment, the present disclosure relates to an electrode sealing assembly designed for use with an electrosurgical instrument for sealing tissue, which includes: first and second jaw members being movable from a first position in spaced relation relative to one another to at least one second position for grasping tissue therebetween. Each of the jaw members includes: an insulating housing having at least one electromechanical interface; and an electrically conductive sealing plate having at least one corresponding electromechanical interface which mates with the electromechanical interface of the insulating housing. The insulating housing has a coolant duct disposed therethrough which is configured to transport a coolant to the insulating housing to dissipate heat away from surrounding tissue.

In another embodiment, the coolant duct is configured to transport the coolant through one or more nozzle(s) disposed on an upper surface of the insulating housing. The nozzle(s) are configured to discharge the coolant to an environment proximate the electrode sealing assembly. In another embodiment, the coolant duct is configured to transport the coolant through the insulating housing to an ultimate heat sink.

BRIEF DESCRIPTION OF THE DRAWINGS

Various embodiments of the subject instrument are described herein with reference to the drawings wherein.

DETAILED DESCRIPTION

Figure 1A:
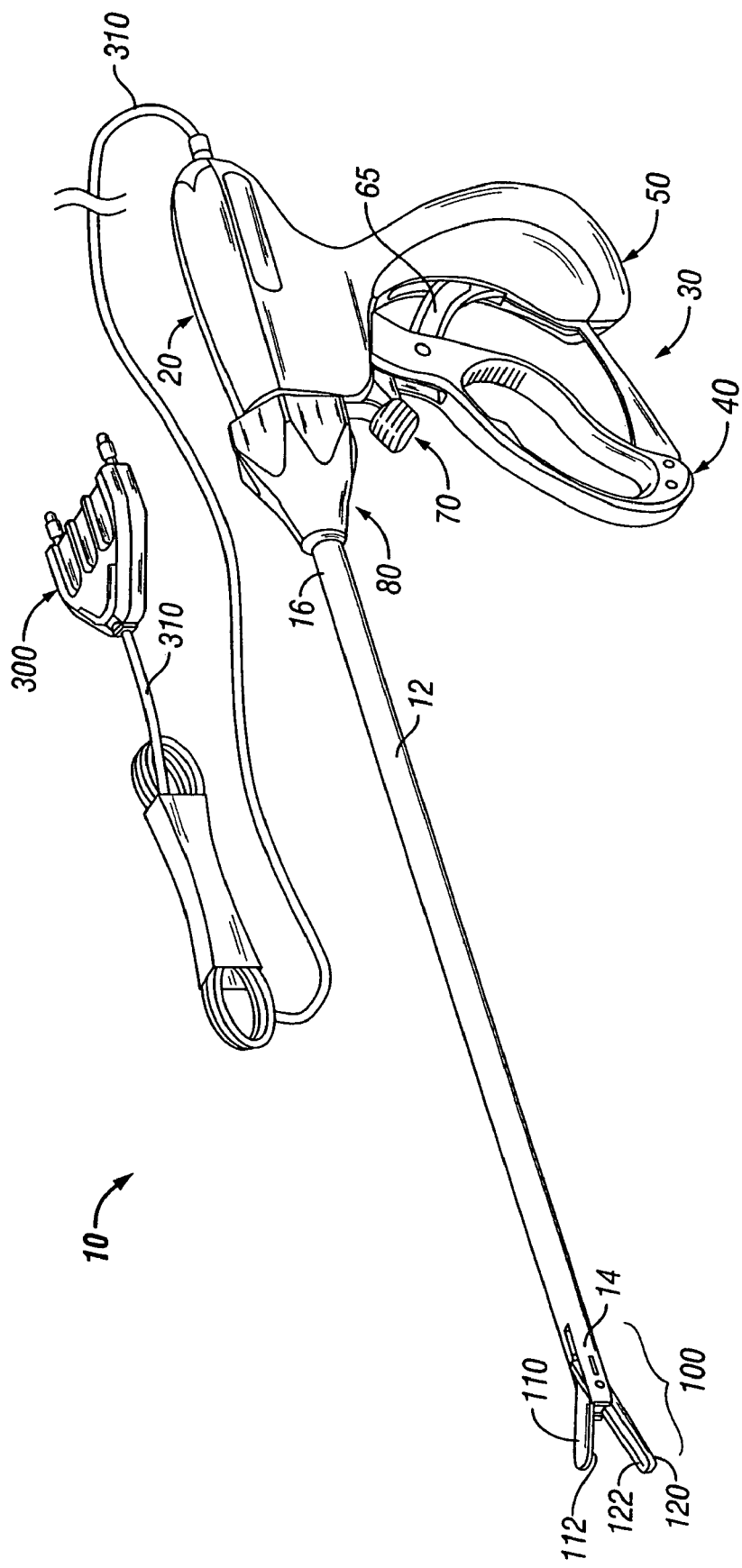
FIG. 1A is a perspective view of an endoscopic bipolar forceps which is configured to support an electrode sealing assembly according to the present disclosure.

It has been found that by providing a thermally conductive and electrically non-conductive material adjacent to the electrically conductive sealing surfaces, surgeons can more readily and more easily produce a consistent, high quality seal and effectively reduce thermal spread across or to adjacent tissue. For the purposes herein the term "thermal spread" refers generally to the heat transfer (heat conduction, heat convection or electrical current dissipation) dissipating along the periphery of the electrically conductive or electrically active surfaces to adjacent tissue. This can also be termed "collateral damage" to adjacent tissue and is further discussed in commonly owned, co-pending PCT Patent Application PCT/US04/13273 entitled "ELECTROSURGICAL INSTRUMENT WHICH REDUCES THERMAL DAMAGE TO ADJACENT TISSUE" which is incorporated herein by reference in its entirety.

It is envisioned that the configuration of the thermally conductive material which surrounds the perimeter of the electrically conductive surface will effectively absorb heat during electrosurgical activation (or thermally dissipate the heat during electrosurgical activation) and generally restrict heat travel to areas between the opposing electrically conductive surfaces. In other words, the material acts like a so called "heat sink". As mentioned above, the thermally conductive material is also electrically non-conductive which also restricts current concentrations to between the two opposing surfaces.

It is important to note that this is different from dielectrically coating the outer surfaces of the instrument to prevent tissue "blanching" at points normal to the sealing site. These coatings are not designed or intended to reduce collateral tissue damage or thermal spread to adjacent tissue (tissue lying along the tissue sealing plane).

It is contemplated that by providing a thermally conductive material adjacent to the electrically conductive surface, the thermally conductive path is altered thereby influencing the thermal spread/collateral damage to adjacent tissue structures. In addition, the thermally conductive, electrically non-conductive material also isolates the two electrically opposing poles (i.e., electrodes) from one another thereby reducing the possibility that tissue or tissue fluids can create an unintended bridge or path for current travel to adjacent tissue. The thermally conductive material and electrically conductive sealing surface may be dimensioned such that the current is concentrated at the intended sealing site between the opposing electrically conductive surfaces as explained in more detail below.

It is contemplated that by providing additional cooling of the electrosurgical jaw members of the bipolar forceps such as by solid state cooling via thermoelectric coolers (TEC) based on the Peltier effect, the thermal spread/collateral damage to adjacent tissue structures may also be further reduced. It is further contemplated that additional cooling may be provided to the electrosurgical jaw members via a cooling duct passing internally through the jaw members.

Figure 1B:
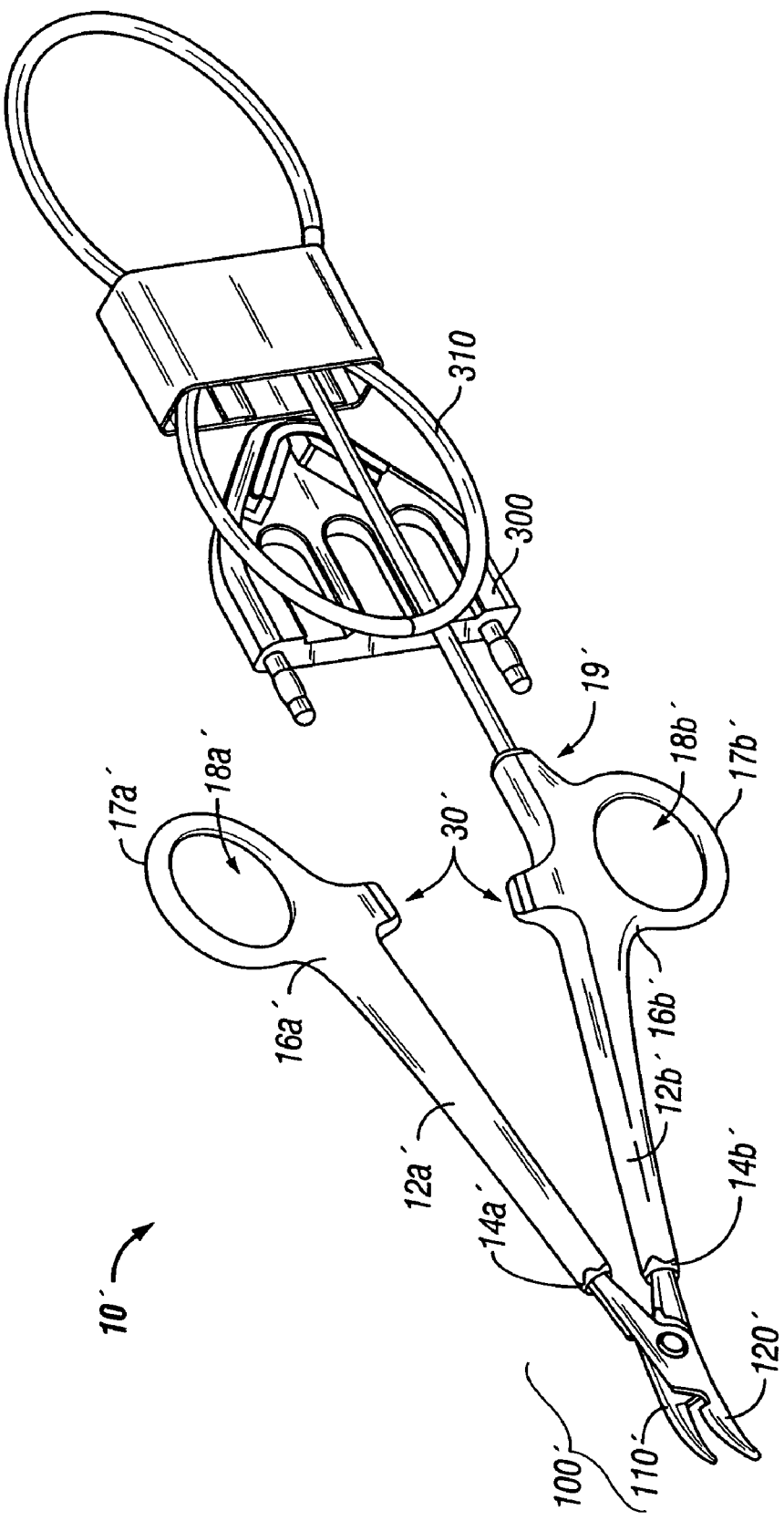
FIG. 1B is a perspective view of an open bipolar forceps which is configured to support the electrode sealing assembly according to the present disclosure.

Referring now to FIGS. 1A and 1B, two bipolar forceps 10 and 10' are shown; a first forceps 10 for use with endoscopic surgical procedures and a second forceps 10' for use with open surgical procedures. For the purposes herein, either an endoscopic instrument or an open instrument may be utilized for supporting the electrode sealing assembly according to the present disclosure. Obviously, different electrical and mechanical connections and considerations apply to each particular type of instrument, however, the novel aspects with respect to the electrode sealing assembly and its operating characteristics remain generally consistent with respect to both the open or endoscopic designs of FIGS. 1A and 1B. Forceps 10 and 10' are shown by way of example and other electrosurgical forceps are also envisioned which may support the electrode sealing assembly of the present disclosure. In the drawings and in the description which follows, the term "proximal", as is traditional, will refer to the end of the forceps 10, 10' which is closer to the user, while the term "distal" will refer to the end which is further from the user.

FIG. 1A shows one example of an endoscopic vessel sealing instrument 10 which is configured to support an electrode sealing assembly 100. More particularly, forceps 10 generally includes a housing 20, a handle assembly 30, a rotating assembly 80, a trigger assembly 70 and the end effector assembly 100 which mutually cooperate to grasp, seal and, if warranted, divide tissue. The forceps 10 includes a shaft 12 which has a distal end 14 dimensioned to mechanically engage the end effector assembly 100 and a proximal end 16 which mechanically engages the housing 20 proximate the rotating assembly 80.

Forceps 10 also includes a plug 300 which connects the forceps 10 to a source of electrosurgical energy, e.g., an electrosurgical generator (not shown) via an electrical cable 310. Handle assembly 30 includes a fixed handle 50 and a movable handle 40. Handle 40 moves relative to fixed handle 50 to actuate the end effector assembly 100 and enable a user to grasp and manipulate tissue 400 (See FIG. 6). More particularly, the end effector assembly 100 includes a pair of opposing jaw members 110 and 120 which move in response to movement of the handle 40 from an open position wherein the jaw members 110 and 120 are disposed in spaced relation relative to one another, to a clamping or closed position wherein the jaw members 110 and 120 cooperate to grasp tissue therebetween.

The housing 20 encloses a drive assembly (not shown) which cooperates with the movable handle 40 to impart movement of the jaw members 110 and 120 from the open position to the clamping or closed position. The handle assembly 30 can generally be characterized as a four-bar mechanical linkage which provides a unique mechanical advantage when sealing tissue between the jaw members 110 and 120. For example, once the desired position for the sealing site is determined and the jaw members 110 and 120 are properly positioned, handle 40 may be compressed fully to lock the jaw members 110 and 120 in a closed position against the tissue. The details relating to the inter-cooperative relationships of the inner-working components of forceps 10 are disclosed in commonly-owned U.S. patent application Ser. No. 10/284,562 and U.S. patent application Ser. No. 10/460,926 which are both incorporated in their entirety by reference herein. When the jaw members 110 and 120 are fully compressed about the tissue, the forceps 10 is now ready for selective application of electrosurgical energy.

Experimental results suggest that the magnitude of pressure exerted on the tissue by the electrically conductive sealing surfaces 112, 122 of the jaw members 110 and 120, respectively, is important in assuring a proper surgical seal. Pressures within a working range of about 3 kg/cm$^2$ to about 16 kg/cm$^2$ and, preferably, within a working range of about 6 kg/cm$^2$ to about 13 kg/cm$^2$ have been shown to be effective for sealing various tissue types. Most preferably, the pressures are within a working range of about 4.5 kg/cm$^2$ to about 8.5 kg/cm$^2$ to optimize sealing.

An open forceps 10' for use in connection with traditional open surgical procedures and is shown by way of example in FIG. 1B. Open forceps 10' includes a pair of elongated shaft portions 12a', 12b' each having a proximal end 16a' and 16b', respectively, and a distal end 14a' and 14b', respectively. The forceps 10' includes jaw assembly 100' which attaches to the distal ends 14a' and 14b' of shafts 12a' and 12b', respectively. Jaw assembly 100' includes an upper jaw member 110' and a lower jaw member 120' which are movable relative to one another to grasp tissue therebetween.

Each shaft 12a' and 12b' may include a handle 17a' and 17b' disposed at the proximal end 16a' and 16b' thereof which each define a finger hole 18a' and 18b', respectively, therethrough for receiving a finger of the user. As can be appreciated, finger holes 18a' and 18b' facilitate movement of the shafts 12a' and 12b' relative to one another which, in turn, pivot the jaw members 110' and 120' from the open position wherein the jaw members 110' and 120' are disposed in spaced relation relative to one another for manipulating tissue to a clamping or closed position wherein the jaw members 110' and 120' cooperate to grasp tissue therebetween.

A ratchet 30' is included for selectively locking the jaw members 110' and 120' relative to one another at various positions during pivoting. Preferably, each position associated with the cooperating ratchet interfaces 30' holds a specific, i.e., constant, strain energy in the shaft members 12a' and 12b' which, in turn, transmits a specific closing force to the jaw members 110' and 120'. It is envisioned that the ratchet 30' may include graduations or other visual markings which enable the user to easily and quickly ascertain and control the amount of closure force desired between the jaw members 110' and 120'. One of the shafts, e.g., 12b', includes a proximal shaft connector Mange 19' which is designed to connect the forceps 10' to a source of RF energy (not shown) via an electrosurgical cable 310 and plug 300. The details relating to the inner-working electrical connections and various components of forceps 10' are disclosed in commonly-owned U.S. patent application Ser. No. 10/369,894 which is incorporated in its entirety by reference herein.

As mentioned above, two mechanical factors play an important role in determining the resulting thickness of the sealed tissue and effectiveness of the seal, i.e., the pressure applied between opposing jaw members 110' and 120' and the gap between the opposing jaw members 110' and 120' during the sealing process. Applying the correct force is also important for other reasons: to reduce the impedance of the tissue to a low enough value that allows enough current through the tissue; and to overcome the forces of expansion during the heating of the tissue in addition to contributing towards creating the required seal thickness necessary for a good seal.

For the purposes herein, electrode assemblies 100 and 100' include the same general configuration and are designed to reduce thermal spread to adjacent tissue. However, certain modifications may have to be made to each electrode sealing assembly 100 (or 100') to fit the electrode sealing assembly 100 (or 100') to a specific support structure for an open or endoscopic instrument. By controlling the intensity, frequency and duration of the RF energy applied to the tissue, the user can selectively seal the tissue as needed for a particular purpose. As can be appreciated, different tissue types and the physical characteristics associated with each tissue type may require different electrical sealing parameters.

Figure 2A:
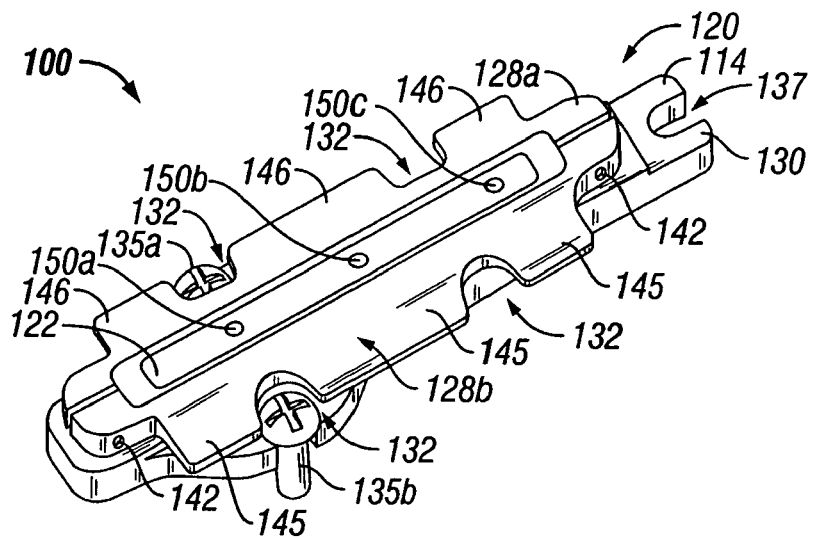
FIG. 2A is an enlarged, perspective view of the electrode sealing assembly according to the present invention.
Figure 2B:
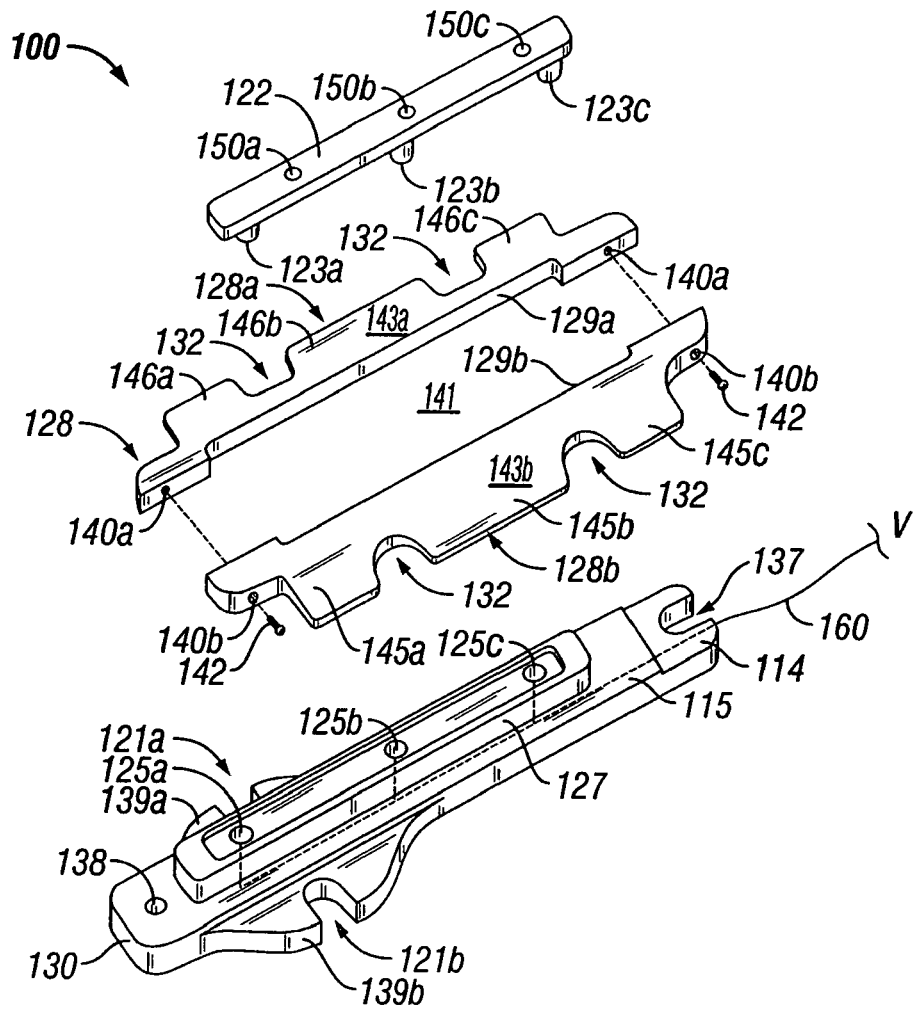
FIG. 2B is an enlarged, perspective view of the embodiment shown in FIG. 2A with parts separated.

FIGS. 2A and 2B show enlarged views of the lower jaw 120 of the electrode sealing assembly 100 (or 100') according to the present disclosure. As can be appreciated a second jaw 110 with similar components as described below is positioned in opposition to jaw member 120. Only the elements of jaw member 120 are described herein, however, jaw member 110 also includes identical or similar elements which are designed to accomplish similar purposes such that bipolar electrosurgical energy can be conducted through tissue held between the two jaw members 110 and 120 to effect a seal.

More particularly, lower jaw member 120 includes an insulated outer housing 114 which supports a thermally conductive, electrically non-conductive material 128 and electrically conductive sealing surface or sealing plate 122. As best seen in FIG. 2B, insulating housing 114 includes a support surface 115 which houses an electrode support step 127. Support step 127 includes a series of electromechanical interfaces 125a, 125b and 125c which matingly engage a set of corresponding interfaces 123a, 123b and 123c which depend from sealing plate 122. The outer periphery of the support step 127 is also preferably dimensioned to matingly engage the thermally conductive material 128 as will be explained in more detail below.

Each electromechanical interface, e.g., 125a, is electrically connected to an electrical potential by way of wire 160 which extends to the generator (not shown). It is envisioned that other electrical configurations are plausible as is known in the art and the above is shown by way of example. For example, electrically conductive tubes or plates may be utilized within the jaw members 110 and 120 to supply current to the sealing plate 122.

Support surface 115 also includes a series of notches 137, 121a, 121b and screw holes 138 which secure the insulating housing 114 to the electrode sealing assembly 100. For example, and as best shown in FIG. 2A, the support surface 115 includes a pair of flanges 139a and 139b which project laterally from the distal end of the support surface 115 and which are each dimensioned to receive the head of a screw 135a and 135b, respectively. In turn, the screws 135a and 135b secure the support surface to the electrode sealing assembly 100. A proximal notch 137 mates with another screw (not shown) to position the end of the support surface 115 on the electrode sealing assembly 100. Other apertures, e.g., 138, may also be utilized to align and/or secure the support surface 115 on the electrode sealing assembly 100 during the manufacturing process.

Thermally conductive material 128 is may be made from two laterally-opposing segments 128a and 128b which mate to encompass the sealing plate 122 and the support step 127 as best seen in FIG. 2A. A series of set screws or pegs 142 secure the two thermally conductive segments 128a and 128b about the sealing plate 122 and about the support step 127 once assembled. As mentioned above, the thermally conductive material 128 is designed to effectively absorb or thermally dissipate the heat during electrosurgical activation and generally restrict heat travel to areas between the opposing sealing plates 122. In other words, the material acts like a "heat sink" to limit thermal damage to surrounding tissue.

As mentioned above, the thermally conductive material 128 is also electrically non-conductive which also restricts current concentrations to between the two opposing sealing plates 122. The thermally conductive material 128 may be made from a material having a high thermal conductivity value or "k" value and minimum electrical conductively, e.g., anodized aluminum. Alternatively, the thermally conductive material 128 may also be made from or combined with a semi-resilient or elastomeric material so as not to inflict mechanical damage to the tissue during compression. Mechanical damage may also be diminished by minimizing the overall tissue contact area of the thermally conductive material 128 (See, e.g., FIG. 3). Alternatively, a spring loaded system (not shown) designed to apply pressures below critical tissue pressure limits may be employed to reduce mechanical damage of the tissue when under compression.

Other compression-reducing systems are also envisioned to avoid over-compression of tissue adjacent the sealing plates 122 and between the opposing thermally conductive materials 128, e.g., rubber-like inserts, foam or the like. Other examples of thermally conductive and electrically non-conductive materials which can be utilized to minimize thermal damage to surrounding tissue include, but are not limited to: thermally conductive plastic materials which dissipate heat along a preferred isothermal profile to the surrounding environment resulting in a lower maximum temperature and reduced formation of hot spots. Examples of such materials are commonly sold under the trademark CoolPoly® by Cool Polymers, Inc., of Rhode Island and composite materials such as $ALO_2$.

As mentioned above, the thermally conductive material 128 includes two segments 128a and 128b which mate about the sealing plate 122 and the support step 127. More particularly, each segment 128a and 128b includes a tissue contacting surface 143a and 143b with a recessed portion 129a and 129b, respectively, along an inner peripheral edge of the tissue contacting surface 143a and 143b such that, once the two segments 128a and 128b are assembled they form a slot 141 for seating the sealing plate 122 therein. The sealing plate 122 is typically seated to lie generally flush with or below the tissue contacting surfaces 143a, 143b of the thermally conductive segments 128a and 128b. It is also envisioned that the thickness (or height relative to the insulating housing 114) of the thermally conductive material 128 proximate the recessed portions 129a, 129b is about equal to the height of the step 127 plus the thickness of the sealing plate 122 such that, once assembled, the sealing plate 122 and the thermally conductive material 128 lie substantially flush or below within the sealing plane.

The thermally conductive segments 128a and 128b may also include a series of fin-like extensions 145a, 145b, 145c and 146a, 146b, 146c, respectively, which extend laterally therefrom. It is envisioned that the fin-like extensions 145a, 145b, 145c and 146a, 146b, 146c further absorb or dissipate heat emanating from the sealing plates 122 during or after activation. The fins 145a, 145b, 145c and 146a, 146b, 146c may also be shaped and dimensioned to facilitate manufacturing and assembly, i.e., the fins 145a, 145b, 145c and 146a, 146b, 146c may be shaped to include slots 132 therein which allow passage of one or more screws 135a, 135b which attach the insulating housing 114 to the underlying electrode sealing assembly 100.

As mentioned above, the sealing plate 122 is electromechanically connected to the underlying insulating housing 114 by virtue of a series of electro-mechanical interfaces 123a, 123b and 123c which project outwardly therefrom to mate with a series of corresponding electromechanical interfaces 125a, 125b and 125c. It is envisioned that the electromechanical interfacing elements 123a, 123b, 123c and 125a, 125b, 125c maintain electrical continuity from the insulating housing 114 to the sealing plate 122. As mentioned above, once assembled and interfaced with the insulating housing 114, the thermally conductive material 128 encapsulates and further secures the sealing plate 122 atop the insulating housing 114.

A series of stop members 150a, 150b and 150c may be disposed on the tissue contacting surfaces or the inner-facing surfaces of the electrically conductive sealing plates 122 (and/or the opposite sealing plate 112 (See FIG. 1A) on jaw member 110) to facilitate gripping and manipulation of tissue and to define a gap distance between opposing jaw members 110 and 120 (or 110' and 120') during sealing. In order to achieve a desired spacing between the electrically conductive plates 112, 122 of the respective jaw members 110, 120, (i.e., gap distance) and apply the required force to properly seal tissue, at least one jaw member 110 or 120 includes at least one stop member or stop members, e.g., 150a, 150b and 150c, which limit the movement of the two opposing jaw members 110 and 120 relative to one another. The stop members, e.g., 150a, extends from the sealing plate or tissue contacting surface 122 a predetermined distance according to the specific material properties of the stop member 150a (e.g., compressive strength, thermal expansion, etc.) to yield a consistent and accurate gap distance during sealing. The gap distance between opposing sealing surfaces 112, 122 (and the sealing surface (not shown) of jaw member 110) during sealing preferably ranges from about 0.001 inches to about 0.006 inches and, preferably, between about 0.002 inches and about 0.003 inches. For larger tissue structures such as bowel, lung or intestine the gap distance ranges from about 0.001 inches to about 0.012 inches and preferably from about 0.005 inches to about 0.007 inches.

Stop members 150a-150c are typically made from an insulative material, e.g., parylene, nylon and/or ceramic. The stop members 150a-150c can be disposed on one or both of the jaw members 110 and 120 and may be dimensioned in a variety of different shapes and sizes, e.g., longitudinal, circular, ridge-like, etc.

The non-conductive stop members 150a-150c are molded onto the sealing plates 112 and 122 (e.g., overmolding, injection molding, etc.), stamped onto the sealing plates 112 and 122, deposited (e.g., plasma deposition) onto the sealing plates 112 and 122 and/or thermally sprayed onto the surface of the sealing plates 112 and 122 (e.g., a ceramic material may be thermally sprayed) to form the stop members 150a-150c. Many different configurations for the stop members 150a-150c are discussed in detail in commonly-assigned, co-pending U.S. Application Serial No. PCT/US01/11413 entitled "VESSEL SEALER AND DIVIDER WITH NON-CONDUCTIVE STOP MEMBERS" by Dycus et al. which is hereby incorporated by reference in its entirety herein.

It is also envisioned that the thermally conductive material 128 may be dimensioned thicker than the height of step 127 and the thickness of the sealing plate 122 such that the thermally conductive material 128 acts like a stop member for maintaining a gap distance between the sealing plates 122 during activation.

In addition to keeping the pressure within a working range (i.e., about 3 kg/cm$^2$ to about 16 kg/cm$^2$) and the gap distance within a specified range (i.e., about 0.001 inches to about 0.012 inches for large tissue structures) the electrical power should be kept within the range of about 1 W to about 350 W, about 1 Vrms to about 400 Vrms and about 0 Amps to about 5.5 Amps.

Thermal spread on each side of the sealing plates 122 is ideally kept to less than about 2 mm and preferably to less than about 0.5 mm to promote tissue healing. However, when sealing larger or well-vascularized tissue structures, thermal spread is acceptable to about 5 mm. It is envisioned that maintaining the viability of tissue surrounding or adjacent the sealing site or fused tissue area will promote healing.

Figure 3:
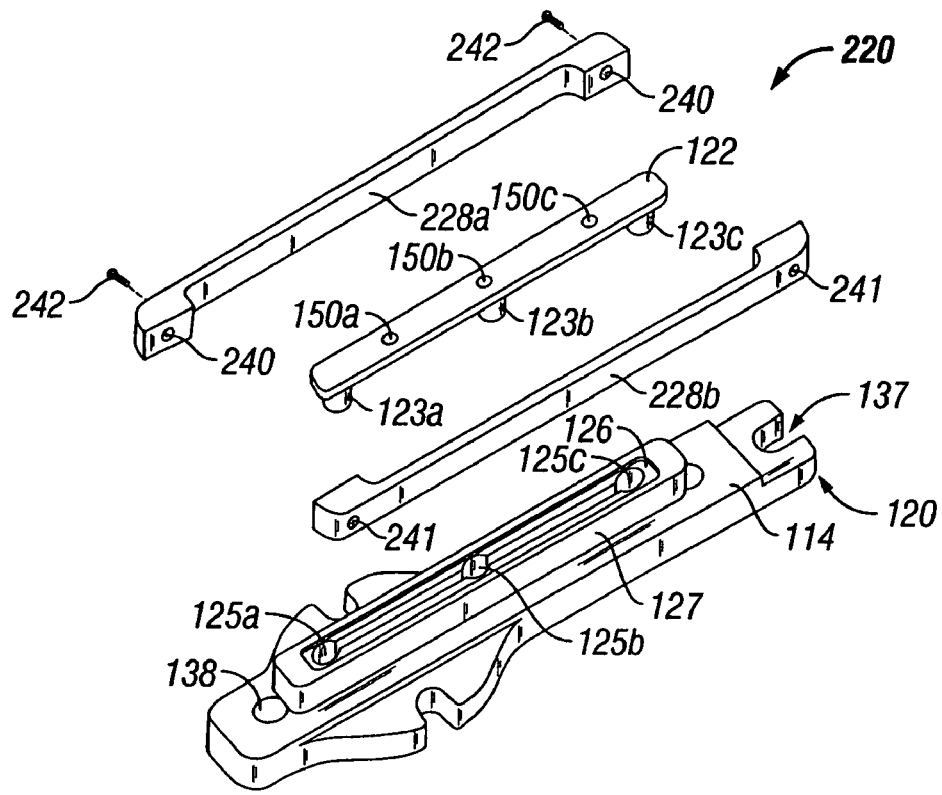
FIG. 3 is an enlarged, perspective view of an alternate, simplified embodiment of the electrode sealing assembly with parts separated according to the present disclosure.
Figure 4:
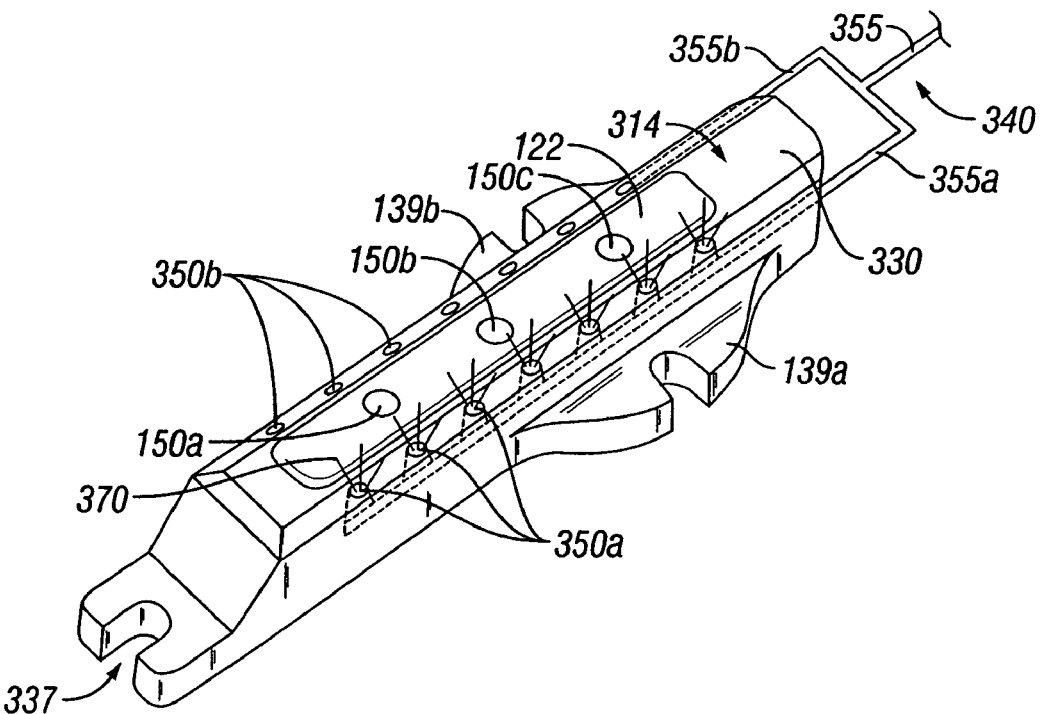
FIG. 4 is an enlarged, perspective view of an alternate embodiment of the electrode sealing assembly showing an active cooling system designed to reduce thermal spread during activation.

FIGS. 3 and 4 show alternate embodiments of lower jaw members 220 and 320 of the electrode sealing assembly 100 which may be utilized to reduce thermal spread to adjacent tissue during activation. More particularly, FIG. 3 shows a lower jaw member 220 which includes the same insulating housing 114 and sealing plate 122 configuration of FIGS. 2A and 2B. The thermally conductive material 228 is modified to have a reduced width which, as mentioned above, reduces the overall tissue contacting surface of the thermally conductive material 128. It is envisioned that mechanical damage may be diminished or at least maintained below critical tissue pressure limits by minimizing the overall tissue contact area of the thermally conductive material 128. Much in the same fashion as described above with respect to FIGS. 2A and 2B, the thermally conductive material 228 is secured about the sealing plate 122 and the step 127 by a series of screws 242 which mate into apertures 240 and 241 in segments 228a and 228b. As can be appreciated, the overall required width of the thermally conductive material 228 may be dependent upon type of tissue being sealed or the thickness of the tissue being sealed. Step 127 may include a reliefed portion 126 disposed therein which seats or aligns the sealing plate 122 during assembly.

FIG. 4 shows yet another possible configuration of the lower jaw member 320 of the electrode sealing assembly 100 (or 100') designed to reduce thermal spread to adjacent tissue. In this embodiment, a thermally conductive material is not utilized as the heat absorbing material or heat sink, but, rather, an active cooling system 340 surrounds the sealing plate 122 to reduce heat dissipation to surrounding tissue. More particularly, insulating housing 314 includes a series of ducts or tubes 355, 355a and 355b disposed therethrough. The coolant ducts 355a, 355b are configured to transport a coolant 370 to the insulating housing 314 to dissipate heat away from surrounding tissue adjacent the sealing plates 122 to actively cool the tissue during activation which reduces thermal spread.

The coolant ducts 355, 355a, 355b supply active cooling liquid (preferably, non-electrically conductive cooling liquid) or gas (e.g., air) 370 through at least one of a series of nozzles or ports 350a and 350b disposed on an upper surface 330 of the insulating housing 314. The nozzles or ports 350a and 350b are located immediately adjacent the sealing plate 122 and extend longitudinally on opposite sides thereof, i.e., ports 350a extend along one side of the sealing plate 122 and ports 350b extend along the opposite side of the sealing plate 122. The nozzles or ports 350a and 350b are configured to discharge the coolant 370 to an environment proximate the electrode sealing assembly 100 (or 100').

As can be appreciated, the sealing system 340 supplies coolant (liquid or gas (e.g., air)) 370 to the tissue areas adjacent the sealing plates 122 to actively cool the tissue during activation which reduces thermal spread. With respect to this particular embodiment and compared to the embodiments of FIGS. 2A-3, the insulating housing 314 encapsulates the sealing plate 122 by virtue of a mechanical connection or manufacturing process, e.g. stamp molding or injection molding.

Figure 5A:
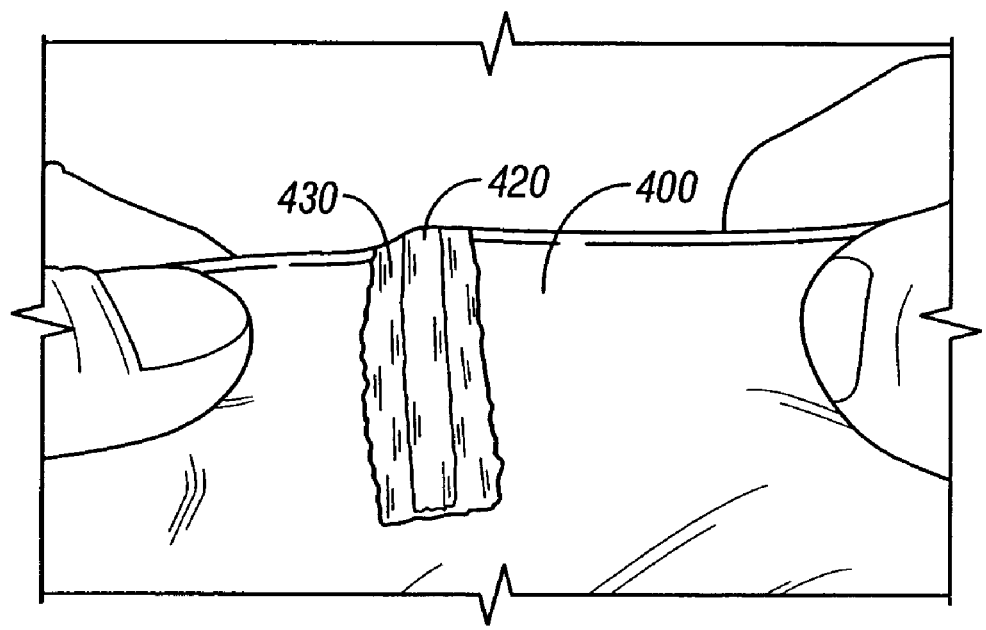
FIG. 5A is an enlarged view of a seal utilizing a conventional vessel sealing instrument with a conventional electrode sealing assembly.
Figure 5B:
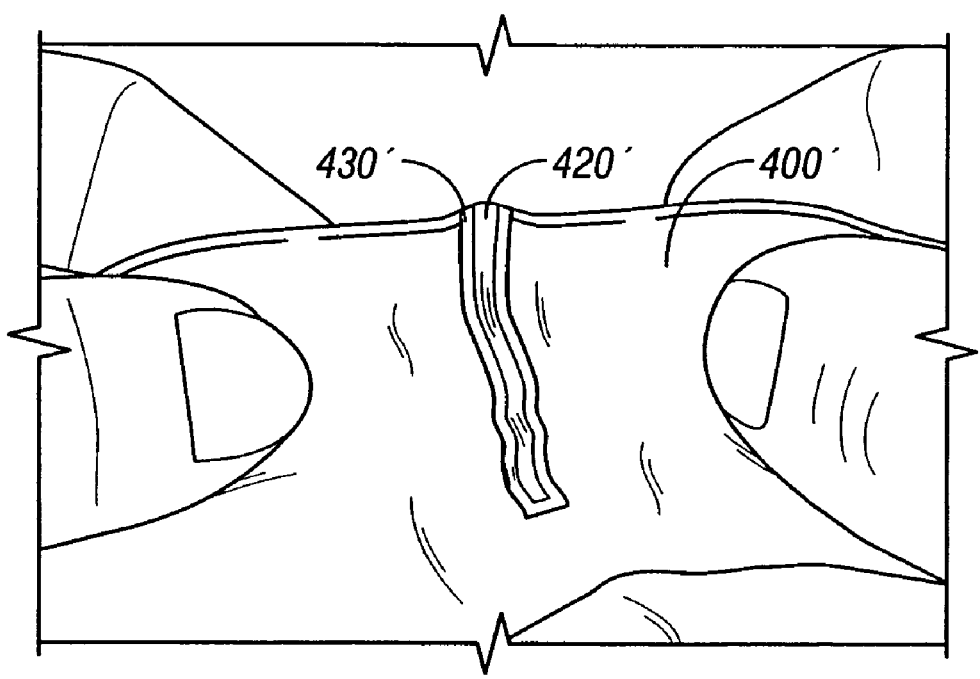
FIG. 5B is an enlarged view of a seal utilizing a vessel sealing instrument having the electrode sealing assembly according the present disclosure.

FIGS. 5A and 5B show a side-by-side comparison of the resulting tissue seals 420 and 420' utilizing a prior vessel sealing instrument (See FIG. 5A) and a vessel sealing instrument designed to reduce thermal spread to adjacent tissue 400 according to the present disclosure (See FIG. 5B). More particularly and with respect to FIG. 5A, there is some notable thermal damage 430 to adjacent tissue 400 proximate the tissue seal 420. FIG. 5B shows the resulting seal 420' utilizing one of the various electrode assemblies 100-(or 100') described herein. A more uniform and narrower seal 420' is evident with a significant reduction of thermal damage 430' to adjacent tissue 400. It is envisioned that reducing thermal damage to adjacent tissue 400 can improve healing especially in sensitive tissue areas, e.g., small and large intestines. As mentioned above, the thermal spread is preferably kept to about 2 mm with sensitive large tissues and vessels and about 5 mm with non-sensitive tissues and vessels.

Figure 6:
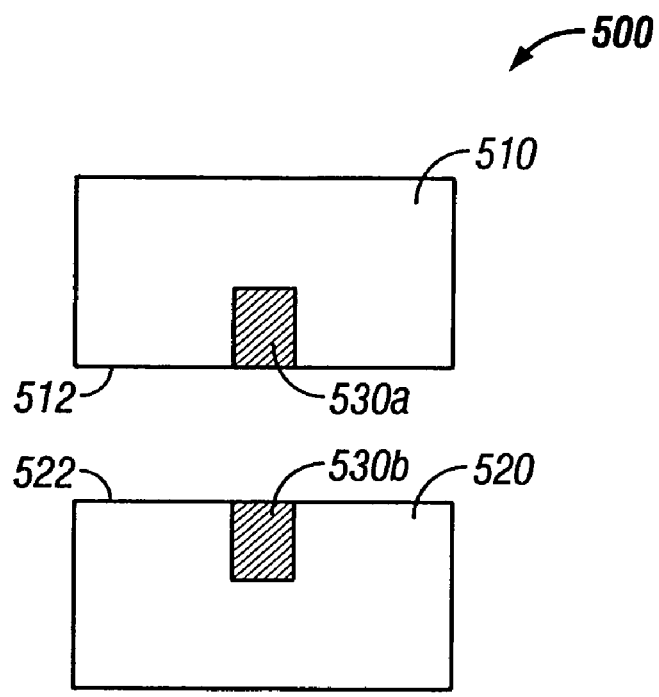
FIG. 6 is a schematic, end view of an alternate electrode sealing assembly which may be utilized to reduce thermal spread during activation.

FIG. 6 shows an alternative electrode sealing assembly 500 which is also designed to reduce thermal spread to adjacent tissue. More particularly, electrode sealing assembly 500 includes upper and lower jaws 510 and 520, respectively, which each include a thermally conductive, electrically insulative material 530a and 530b, e.g., a so-called "cool polymer" material, disposed on (or within) the respective tissue sealing plates, 512 and 522. The cool polymers 530a, 530b may be centrally disposed within each sealing plate 512 and 522, respectively. It is envisioned that the cool polymers 530a and 530b will act as heat sinks (i.e., absorb heat) during activation which will limit the thermal spread to adjacent tissue 400. Examples of cool polymers include thermally conductive plastic materials which dissipate heat in a more isothermal profile to the surrounding environment resulting in a lower maximum temperature and reduced formation of hot spots such as materials commonly sold under the trademark CoolPoly® by Cool Polymers, Inc., of Rhode Island. Alternatively, certain known ceramic materials may also be used to reduce tissue effects.

Figure 7:
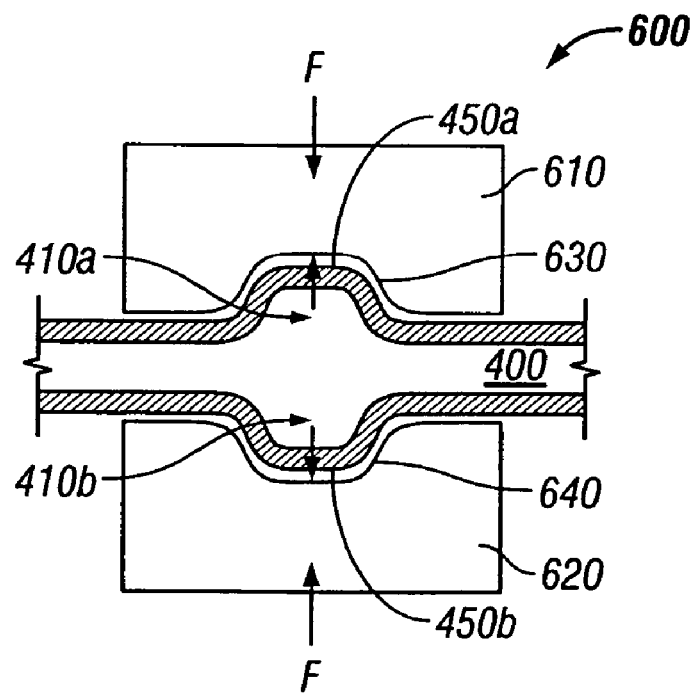
FIG. 7 is a schematic, end view of another alternate electrode sealing assembly which may be utilized to reduce thermal spread during activation.

FIG. 7 shows yet another electrode sealing assembly 600 which is also designed to reduce thermal spread to adjacent tissue 400. More particularly, electrode sealing assembly 600 includes upper and lower jaw members 610 and 620, respectively which are designed to engage tissue 400 therebetween. Each of the jaw members 610 and 620 includes a recessed portion 630 and 640, respectively which is dimensioned to allow bulging portions 450a and 450b of the tissue 400 to bulge into each respective jaw member 610 and 620 when the tissue 400 is under compression. It is envisioned that the moisture in the less-compressed tissue bulges 450a and 450b essentially acts as a heat sink to absorb heat during activation and reduce thermal spread to surrounding tissue.

It is envisioned that the jaw members 110 and 120 may be curved in order to reach specific anatomical structures and promote more consistent seals for certain procedures. For example, it is contemplated that dimensioning the jaw members 110 and 120 at an angle of about 45 degrees to about 70 degrees is preferred for accessing and sealing specific anatomical structures relevant to prostatectomies and cystectomies, e.g., the dorsal vein complex and the lateral pedicles. Other angles may be preferred for different surgical procedures.

Figure 8A:
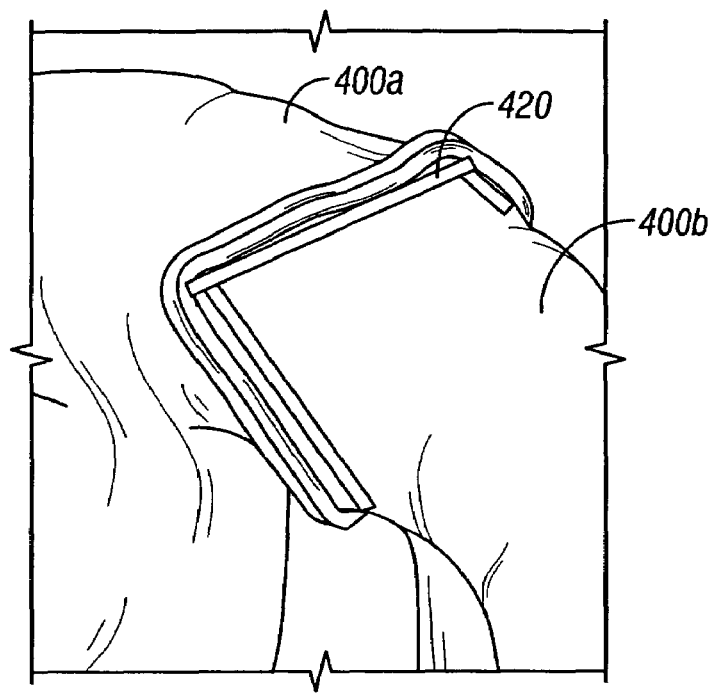
FIG. 8A shows a perspective view of a sealed tissue area of an end-to-end anastomosis utilizing a straight electrode sealing assembly according to the present disclosure.
Figure 8B:
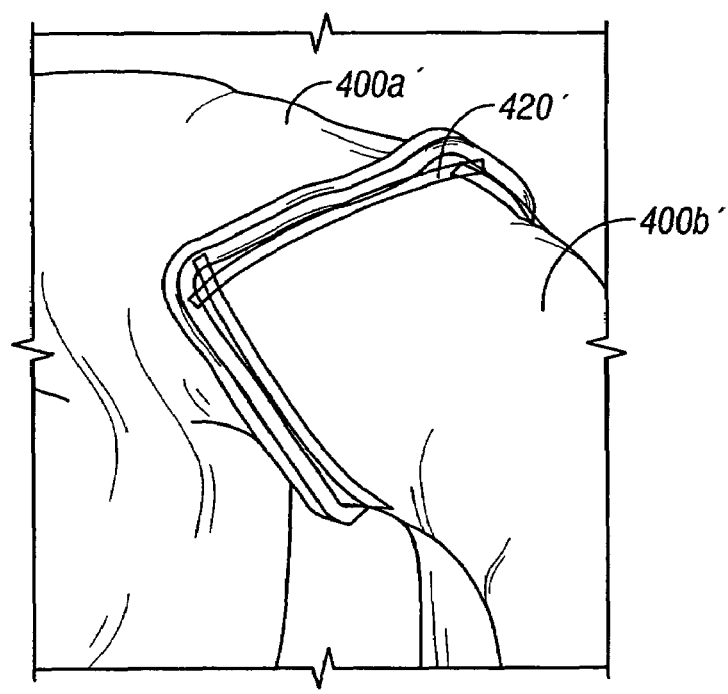
FIG. 8B shows a perspective view of a sealed tissue area of an end-to-end anastomosis utilizing a curved electrode sealing assembly according to the present disclosure.

For example and as best shown in FIGS. 8A and 8B, it may be preferable to use a curved jaw member (not shown) for an end-to-end anastomosis of bowel tissues. FIG. 8A shows the resulting seal 420 of an end-to-end anastomosis of two bowel segments 400a and 400b utilizing a straight pair of jaw members. FIG. 8B shows a resulting seal 420' of an end-to-end anastomosis of two bowel segments 400a' and 400b' utilizing a curved pair of jaw members. As can be appreciated the resulting seal 420' from the curved pair of jaw members tends to more closely conform to the general contours of the two tissue segments 400a' and 400b' which is envisioned will promote tissue healing around the anastomosis site.

It is also envisioned that the jaw members 110 and 120 may be tapered which is advantageous for two reasons: 1) the taper will apply constant pressure for a constant tissue thickness at parallel; 2) the thicker proximal portion of each jaw member 110 and 120 will resist bending due to the reaction force of the tissue 400.

It is also envisioned that the above forceps 10 (or 10') may be utilized in connection with a closed-loop RF control system which optimizes sealing based upon pre-surgical conditions or changes in physical or electrical conditions during sealing. One example of a closed-loop control system is described in commonly-owned U.S. patent application Ser. No. 10/427,832 filed on May 1, 2003 entitled "METHOD AND SYSTEM FOR CONTROLLING OUTPUT OF RF MEDICAL GENERATOR" and commonly-owned U.S. patent application Ser. No. 10/835,657 filed on Apr. 30, 2004 entitled "METHOD AND SYSTEM FOR PROGRAMMING AND CONTROLLING AN ELECTROSURGICAL GENERATOR SYSTEM" which are both incorporated in their entirety by reference herein. In general, the closed-loop control, system includes a user interface for allowing a user to select at least one pre-surgical parameter, such as the type of surgical instrument operatively connected to the generator, the type of tissue and/or a desired surgical effect. A sensor module is also included for continually sensing at least one of electrical and physical properties proximate the surgical site and generating at least one signal relating thereto.

The closed loop control system also includes a control module for continually receiving or monitoring surgical parameters and each of the signals from the sensor module and processing each of the signals in accordance with a desired surgical effect using a microprocessor, computer algorithm and/or a look-up table. The control module generates at least one corresponding control signal relating to each signal from the sensor module(s), and relays the control signal to the electrosurgical generator for controlling the generator. The closed loop system may be employed in a feedback circuit or part of a surgical method for optimizing a surgical seal. The method includes the steps of: applying a series of electrical pulses to the surgical site; continually sensing electrical and physical properties proximate the surgical site; and varying pulse parameters of the individual pulses of the series of pulses in accordance with the continually-sensed properties. Alternatively, the signal may be continuous.

It is also contemplated that the sealing surfaces 122 of the jaw members 110 and 120 can be made from or coated with non-stick materials to reduce tissue adhesion. Alternatively, the jaw members 110 and 120 may be surface treated, roughened, to reduce sticking, e.g., bead blasting, stamping. When utilized on the sealing surfaces 122, these materials provide an optimal surface energy for eliminating sticking due in part to surface texture and susceptibility to surface breakdown due to electrical effects and corrosion in the presence of biologic tissues. It is envisioned that these materials exhibit superior non-stick qualities over stainless steel and should be utilized on the forceps 10 (or 10') in areas where the exposure to pressure and RF energy can create localized "hot spots" more susceptible to tissue adhesion. As can be appreciated, reducing the amount that the tissue "sticks" during sealing improves the overall efficacy of the instrument. Controlling tissue cooling may also reduce adhesion or buildup of tissue on the electrodes and also assist during the formation of the tissue seal, e.g., cross-linking or other chemical bonding, during the reformation or renaturation of collagen.

The non-stick materials may be manufactured from one (or a combination of one or more) of the following "non-stick" materials: nickel-chrome, chromium nitride, MedCoat 2000, Inconel 600, tin-nickel or various nitride coatings which include, but are not limited to, TiN, ZrN, TiAlN and CrN. For example, high nickel chrome alloys, Ni200, Ni201 (~100% Ni) may be made into electrodes or sealing surfaces by metal injection molding, stamping, machining or any like process. Also and as mentioned above, the sealing surfaces 122 may also be "coated" with one or more of the above materials to achieve the same result, i.e., a "non-stick surface".

It is further envisioned that thermal spread may be reduced by altering the physical dimensions of the insulating housing 114. For example, in some cases it may be preferable to manufacture the insulating housing 114 from a variety of materials (either alone or in combination) which include: nylons and syndiotactic polystryrenes such as QUESTRAe manufactured by DOW Chemical; Polybutylene Terephthalate (PBT); Polycarbonate (PC); Acrylonitrile Butadiene Styrene (ABS); Polyphthalamide (PPA); Polymide, Polyethylene Terephthalate (PET); Polyamide-imide (PAI); Acrylic (PMMA); Polystyrene (PS and HIPS); Polyether Sulfone (PES); Aliphatic Polyketone; Acetal (POM) Copolymer; Polyurethane (PU and TPU); Nylon with Polyphenylene-oxide dispersion; and Acrylonitrile Styrene Acrylate.

It is also contemplated that only one of the two jaw members 110 and 120 may include one of the aforedescribed mechanisms or configurations for reducing thermal spread. For example and with reference to FIGS. 2A, 2B and 3, it is contemplated that only the lower jaw member 120, 220 may include the thermally conductive material 128, 228 disposed between the insulating housing 114 and the sealing plate 122. With reference to FIG. 4, only the lower jaw member 320 may include the active cooling system 340. With reference to FIG. 6, only the top jaw member 510 may be configured to house a cool polymer 530a for reducing thermal spread to adjacent tissue 400. Likewise and with reference to FIG. 7, only the upper jaw member 610 may include a recessed area 630 for receiving bulging tissue 450a. It is further contemplated that the above configurations may be used in combination to reduce thermal spread to adjacent tissue. For example, a cool polymer 530a may be used in combination with the thermally conductive material 128 of FIG. 2A or used in replace of the thermally conductive material 128 of FIG. 2A depending upon a particular purpose.

It is envisioned that the forceps 10 or 10' may be designed such that it is fully or partially disposable depending upon a particular purpose or to achieve a particular result. For example, electrode sealing assembly 100 may be selectively and releasably engageable with the distal end 14 of the shaft 12 and/or the proximal end 16 of shaft 12 may be selectively and releasably engageable with the housing 20 and the handle assembly 30. In either of these two instances, the forceps 10 would be considered "partially disposable" or "reposable", i.e., a new or different electrode sealing assembly 100 (or electrode sealing assembly 100 and shaft 12) selectively replaces the old jaw assembly 110 as needed.

Figure 9A:
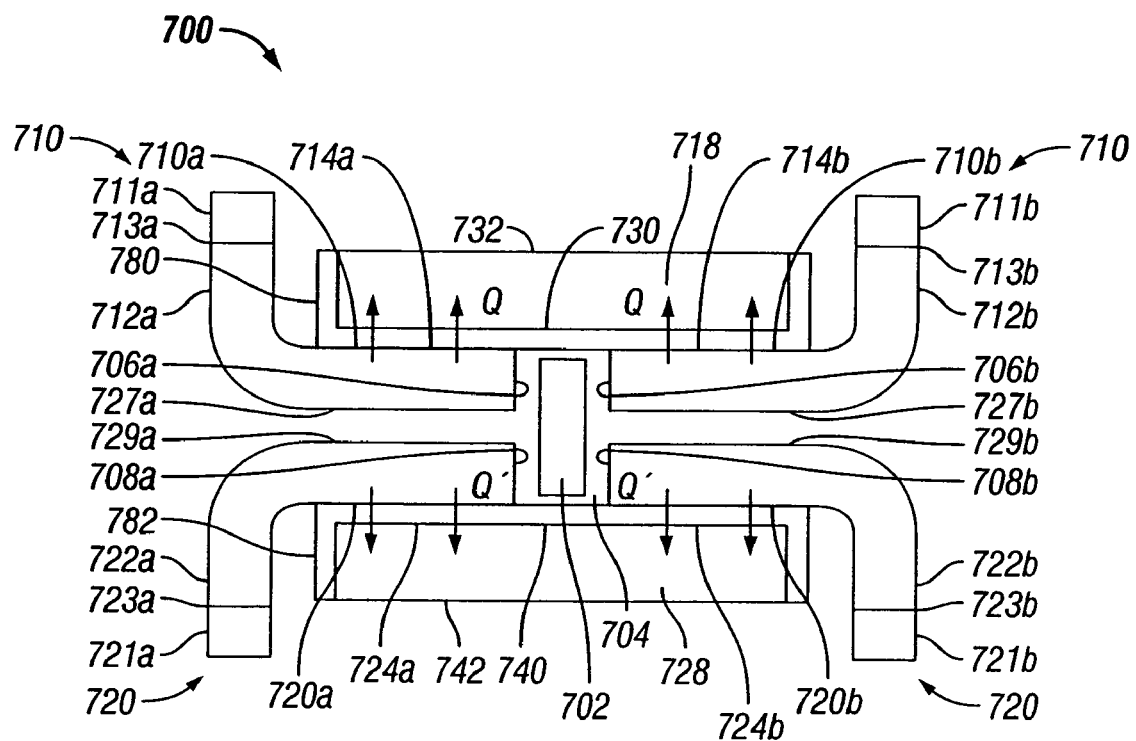
FIG. 9A shows an end view of the jaw members of an electrode sealing assembly which are configured to support an alternate embodiment of an electrode cooling assembly according to the present disclosure.

Another embodiment of an electrode cooling system for an electrode assembly 700 according to the present disclosure is illustrated in FIG. 9A. More particularly, FIG. 9A shows an end view of a distal end of lower electrode jaw member 720 and a distal end of upper electrode jaw member 710 of electrode assembly 700 adapted for use as a bipolar forceps 10. The upper electrode jaw member 710 includes upper electrically insulating portions 711a, 711b joined at edges 713a, 713b to contact electrically conductive seal plates 712a, 712b. The lower electrode jaw member 720 includes lower electrically insulating portions 721a, 721b joined at edges 723a, 723b to contact electrically conductive seal plates 722a, 722b. A knife blade 702 is shown disposed within a knife slot 704 formed by inward lateral side edges 706a and 706b of the electrically conductive seal plates 712a and 712b and by inward lateral side edges 708a and 708b of the electrically conductive seal plates 722a and 722b. The jaw members 710 and 720 have a generally U-shaped cross-section with a generally flat central portion 710a, 710b, 720a, 720b, in the electrically conductive seal plates 712a, 712b, and 722a, 722b, respectively.

During the tissue sealing process, heat Q is generated on inner surface 727a, 727b in the generally flat central portion 710a, 710b of electrically conductive seal plates 712a and 712b. Similarly, heat Q' is generated on inner surface 729a, 729b in the generally flat central portion 720a, 720b of electrically conductive seal plates 722a and 722b.

At least one of the jaw members 710 and 720 includes a thermoelectric plate such that heat generated by at least one of the jaw members is transferred away from the tissue via the thermoelectric plate. More particularly, a first surface 730 of an upper thermoelectric (TEC) plate 718 and an outer surface 714a, 714b of the upper electrically conductive seal plates 712a, 712b in the generally flat central portion 710a, 710b have a thermally conductive, electrically insulating material 780 disposed therebetween. Correspondingly, a first surface 740 of a lower thermoelectric (TEC) plate 728 and an outer surface 724a, 724b of the lower electrically conductive seal plates 722a, 722b in the generally flat central portion 720a, 720b have a thermally conductive, electrically insulating material 782 disposed therebetween.

The heat Q generated on inner surface 727a, 727b of upper jaw member 710 is transferred through the upper electrically conductive seal plates 712a, 712b and through the thermally conductive, electrically insulating material 780 to the first surface 730 of the upper TEC plate 718 where the heat Q is transferred to the TEC plate 718.

Similarly, the heat Q generated on inner surface 729a, 729b of upper jaw member 720 is transferred through the lower electrically conductive seal plates 722a, 722b and through the thermally conductive, electrically insulating material 782 to the first surface 740 of the lower TEC plate 728 where the heat Q is transferred to the TEC plate 728.

It is contemplated that in most cases of electrosurgery, both of the jaw members 710 and 720 would include their respective TEC plates 718 and 728 for cooling purposes. Furthermore, those skilled in the art will recognize that TEC plates 718 and 728 may be alternatively referred to as solid state heat pumps or Peltier coolers.

Figure 9B:
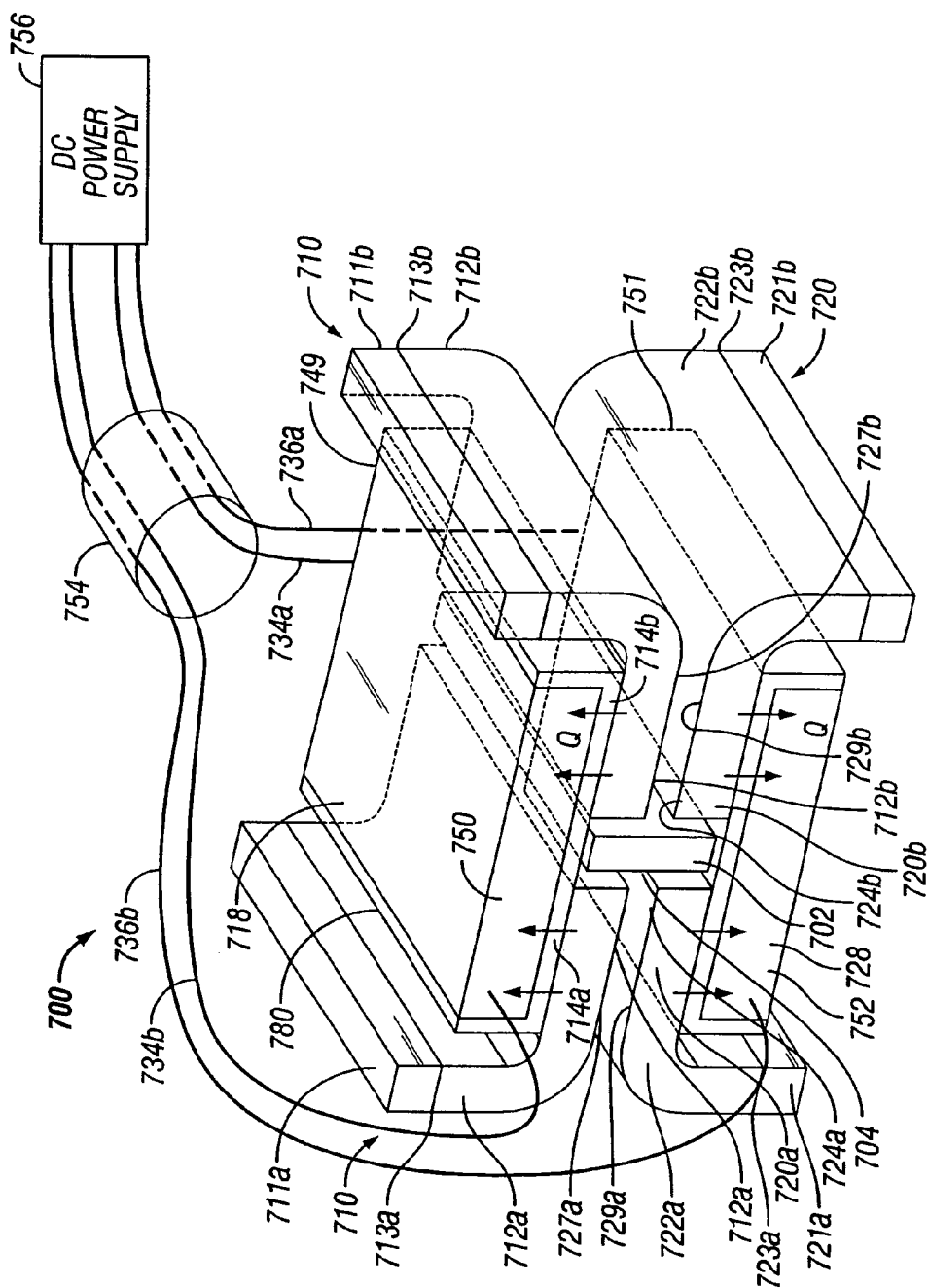
FIG. 9B shows a perspective view of the jaw members according to FIG. 9A.

As shown in FIG. 9B, electrical lead 734a is connected to a proximal end 749 of upper TEC plate 718, while electrical lead 734b is connected to a distal end 750 of upper TEC plate 718. Similarly, electrical lead 736a is connected to a proximal end 751 of lower TEC plate 728, while electrical lead 736b is connected to a distal end 752 of lower TEC plate 728. The leads 734a, 734b, 736a, 736b are routed through a conduit or cable 754 to a direct current (DC) power supply 756. As noted previously, during the tissue sealing process, heat Q is generated on inner surface 727a, 727b in the generally flat central portion 710a, 710b of upper seal plates 712a, 712b. Similarly, heat Q' is generated on inner surface 729a, 729b in the generally flat central portion 720a, 720b of lower seal plate 722a, 722b.

The TEC plates 718 and 728 provide the capability of directing this heat Q away from the inner surfaces 727a, 727b and 729a, 729b depending upon direction of current flow through the electrical leads. In most cases of electrosurgery, the TEC plates would be used for cooling rather than heating. To achieve cooling, direction of current is controlled by the power supply 756 and current is directed through the TEC plates 718 and 728 such that the heat Q from the seal plates 712a, 712b, 722a, 722b is directed away from the tissue and towards the opposite end of the TEC plates 718 and 728. As can be appreciated, the heat Q generated during tissue sealing by the electrodes 710 and 720 is transferred away from the tissue and is not transmitted to surrounding tissue, thus reducing collateral damage to tissue. The thermally conductive, electrically insulating materials 780, 782 may be made of a cool polymer as described previously which prevents electrical continuity between the DC power supply 756 and an AC power supply from the previously discussed source of electrosurgical energy e.g., an electrosurgical generator (not shown) via plug 300 and electrical cable 310 (see FIGS. 1A and 1B).

Figure 9C:
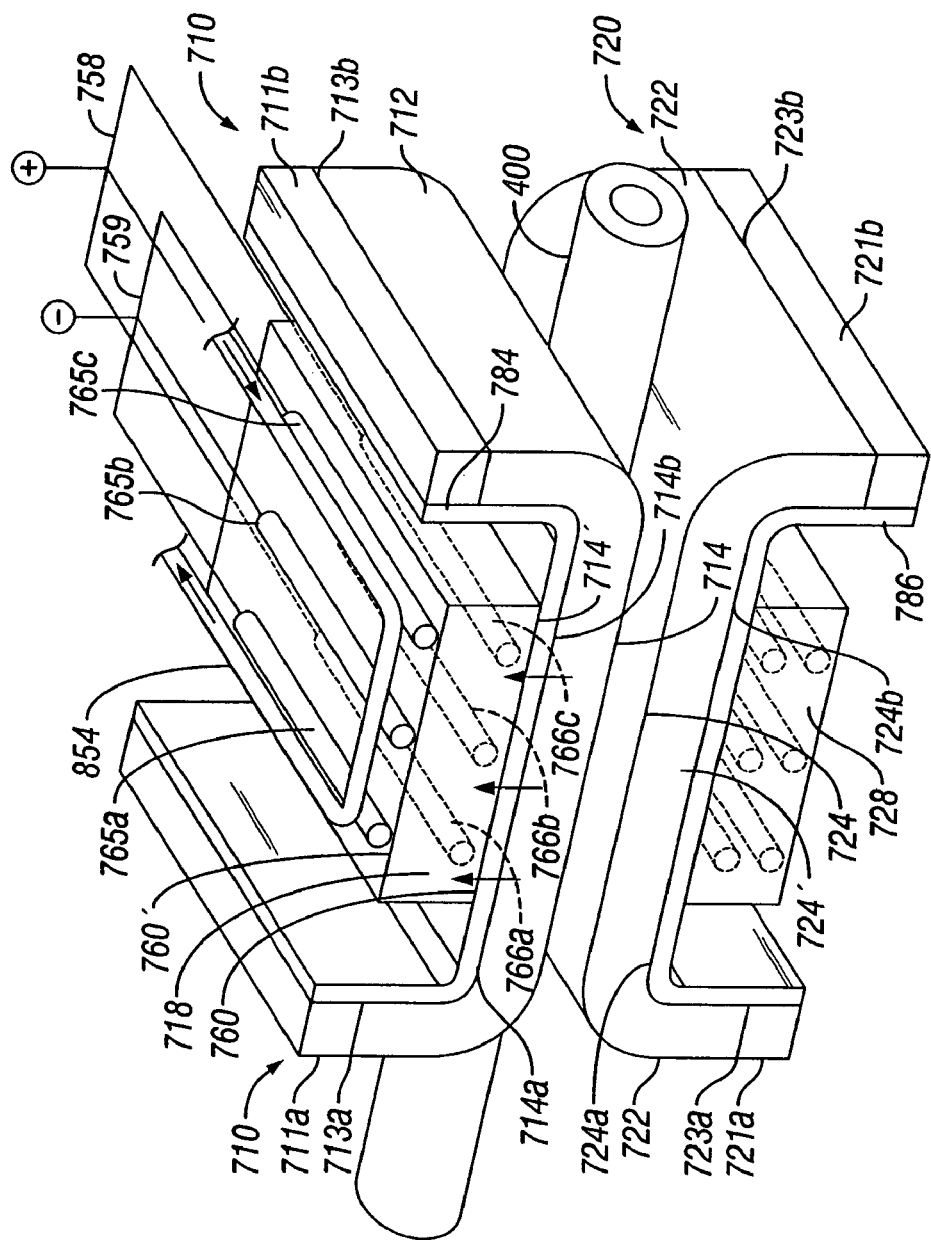
FIG. 9C shows a top perspective view of the jaw members of an electrode sealing assembly which are configured to support still another embodiment of an electrode cooling assembly according to the present disclosure.
Figure 9D:
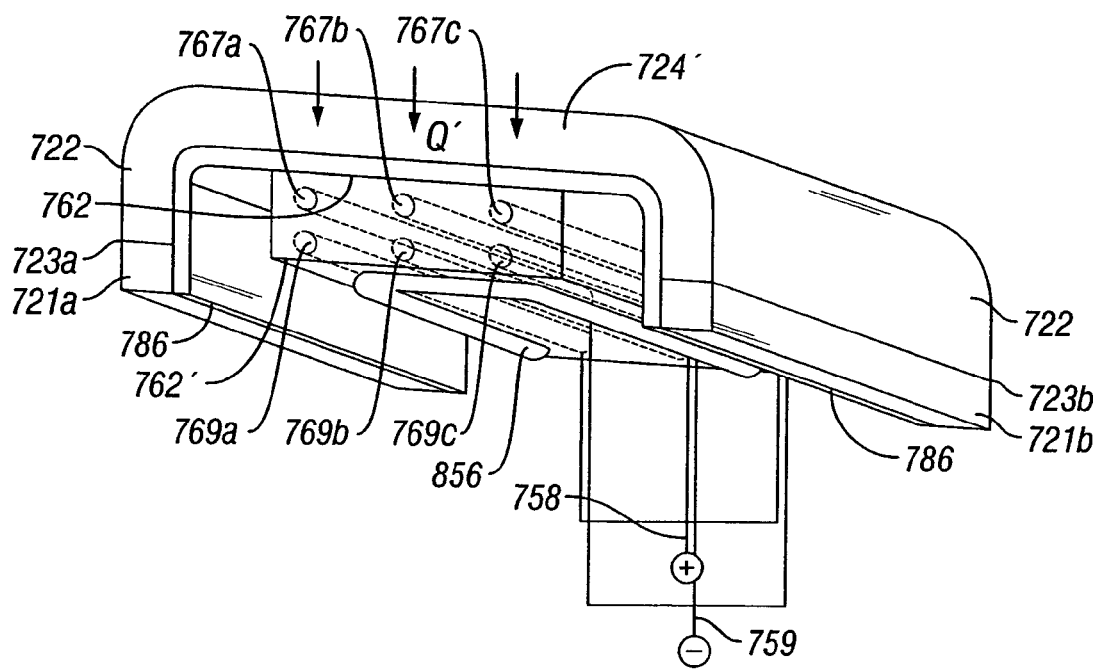
FIG. 9D shows a bottom perspective view of the jaw members according to FIG. 9C.

FIGS. 9C and 9D show one particularly useful embodiment according to the present disclosure wherein TEC plate 718 is utilized to dissipate heat from the jaw members 710 and 720 during tissue treatment. More particularly, and with specific reference to jaw member 710, the jaw member 710 includes upper electrically insulating portions 711a and 711b joined at edges 713a, 713b to contact an electrically conductive seal plate 712. TEC plate 718 is disposed within jaw member 710 on the opposite side 714' of tissue engaging surface 714 of the electrically conductive sealing plate 712. A thermally conductive, electrically insulating material 784 is disposed between the TEC sealing plate 718 and sealing plate 712 on outer surfaces 714a and 714b of the sealing plate 712. The plate 718 includes first and second sides 760 and 760', respectively. Side 760 abuts the opposite end 714' of sealing plate 712. A series of electrical leads 765a, 765b, and 765c are connected to the second side 760' while a series of electrical leads 766a, 766b, and 766c are connected to the first side 760.

It is envisioned that a first electrical potential 758 may be selectively transmitted through leads 765a, 765b and 765c and a second electrical potential 759 may be selectively transmitted through leads 766a, 766b, and 766c such that different electrical potentials are created on opposite sides of the plate 718. As can be appreciated, heat Q in this instance may be directed proximally for absorption by a second heat sink, e.g., cool polymer, a fluid through one or more ducts 854 disposed in contact with TEC plate 718, or another TEC plate.

Jaw member 720 is configured in much the same manner and includes similar elements for directing heat Q proximately. More particularly, and with specific reference to jaw member 720, the jaw member 720 includes lower electrically insulating portions 721a and 721b joined at edges 723a, 723b to contact an electrically conductive seal plate 722. TEC plate 728 is disposed within jaw member 720 on the opposite side 724' of tissue engaging surface 724 of the electrically conductive sealing plate 722. A thermally conductive, electrically insulating material 786 is disposed between the sealing plate 722 and the TEC plate 728 on outer surfaces 724a and 724b of the sealing plate 722. The plate 728 includes first and second sides 762 and 762', respectively. Side 762 abuts the opposite end 724' of sealing plate 722. A series of electrical leads 767a, 767b, and 767c are connected to the first side 762 while a series of electrical leads 769a, 769b and 769c are connected to the second side 762'.

The thermally conductive, electrically insulating materials 784, 786 may be made of a cool polymer as described previously which prevents electrical continuity between the DC power supply 756 and an AC power supply from the previously discussed source of electrosurgical energy.

It is envisioned that first electrical potential 758 may be selectively transmitted through leads 767a, 767b and 767c and second electrical potential 759 may be selectively transmitted through leads 769a, 769b, and 796c such that different electrical potentials are created on opposite sides of the plate 728. As can be appreciated, heat Q' in this instance may be directed proximally for absorption by a second heat sink, e.g., cool polymer, a fluid through one or more ducts 856 disposed in contact with TEC plate 728, or another TEC plate. As can be appreciated, the two jaw members 710, 720 cooperate to remove excess heat from the tissue to reduce collateral tissue effects during sealing.

Figure 10A:
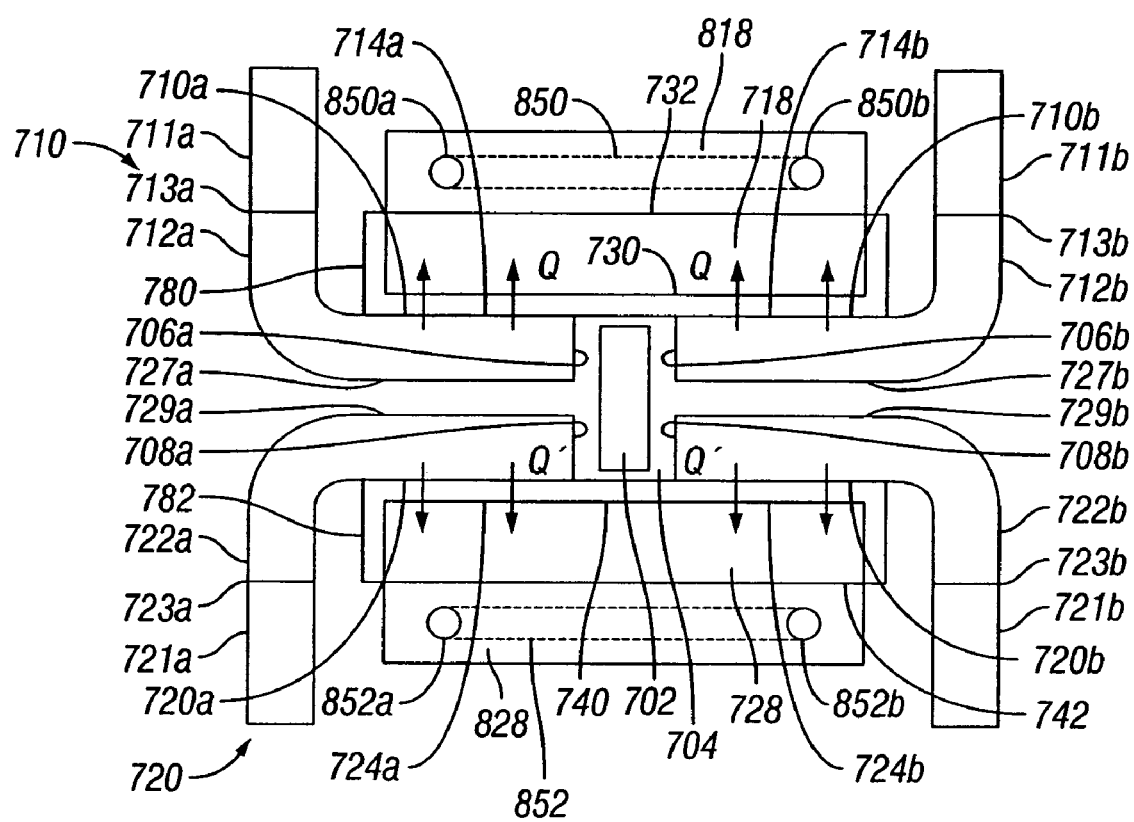
FIG. 10A shows an end view of jaw members of an electrode sealing assembly which are configured to support yet another alternate embodiment of an electrode cooling assembly according to the present disclosure.

FIG. 10A shows a proximal end of the electrode assembly 700 configured in one particularly useful embodiment for forced convection cooling of the upper electrode jaw members 710 and lower electrode jaw members 120. FIG. 10A is in all respects identical to FIG. 9A except that electrode assembly 700 is configured for forced convection cooling of the upper seal plates 712a, 712b and lower seal plates 722a, 722b. More particularly, a heat sink 818 is disposed in direct contact with a second surface 732 of thermoelectric cooling plate 718. A coolant or cooling line 850 is disposed through or embedded within heat sink 818. The coolant line 850 has a coolant supply end 850a and a coolant return end 850b projecting from a proximal end of the heat sink 818.

Similarly, a heat sink 828 is disposed in direct contact with a second surface 742 of thermoelectric cooling plate 728. A coolant or cooling line 852 is disposed through or embedded within heat sink 828. The coolant line 852 has a coolant supply end 852a and a coolant return end 852b projecting from a proximal end of the heat sink 828.

Figure 10B:
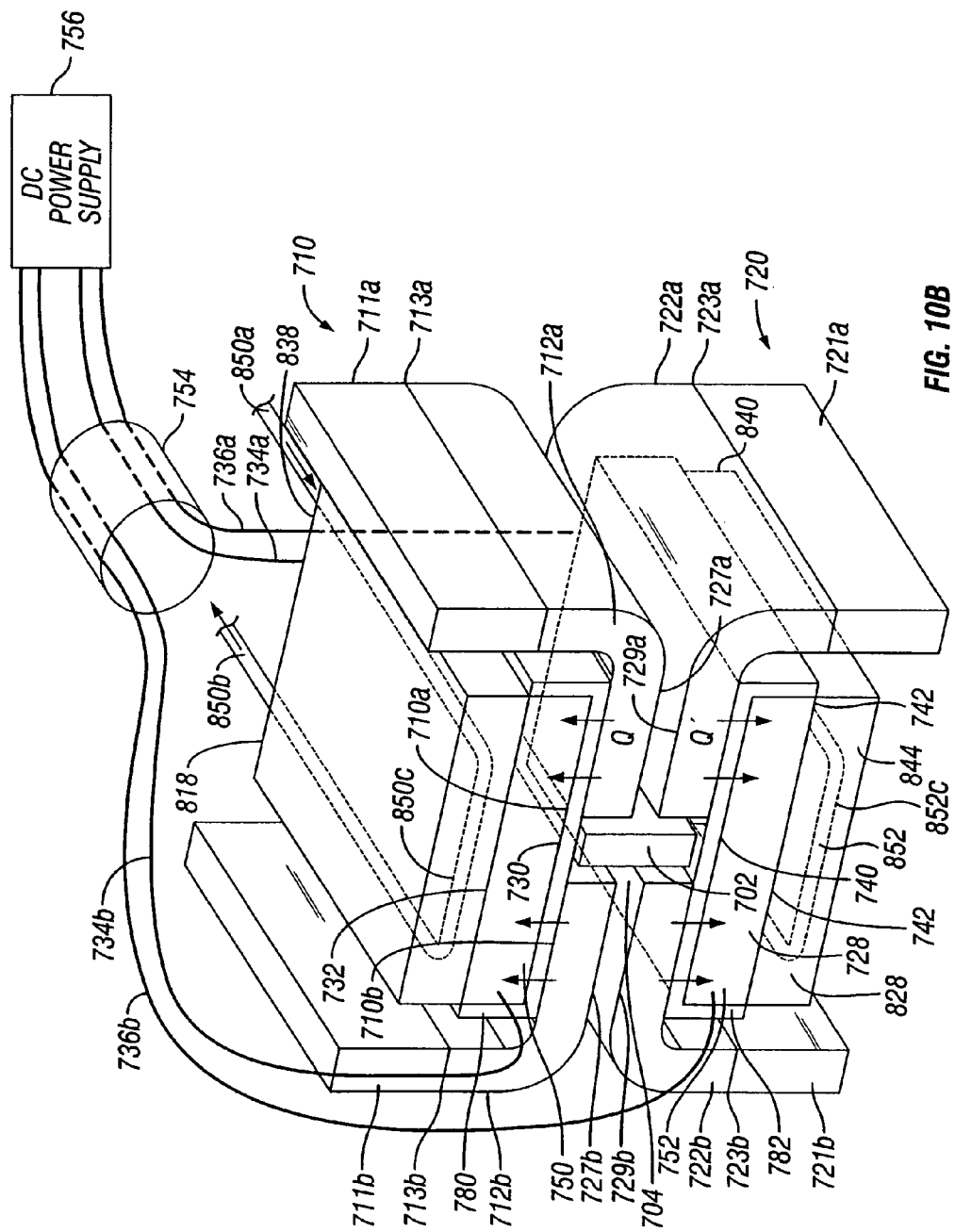
FIG. 10B shows a perspective view of the jaw members according to FIG. 10A.

FIG. 10B shows a front perspective view of the electrode assembly 700 of FIG. 10A as configured for forced convection cooling of the upper seal plates 712a, 712b and lower seal plates 722a, 722b. More particularly, the heat sink 818 is disposed in direct contact with the second surface 732 of thermoelectric cooling plate 718. The coolant line 850 is disposed through or embedded within heat sink 818. The coolant line 850 has coolant supply end 850a and coolant return end 850b projecting from a proximal end 838 of the heat sink 818. The coolant line 850 may form a U-bend 850c proximate to a distal end 842 of heat sink 818.

Similarly, heat sink 828 is disposed in direct contact with the second surface 742 of thermoelectric cooling plate 728. The coolant line 852 is disposed through or embedded within heat sink 828. The coolant line 852 has a coolant supply end (not shown) and a coolant return end (not shown) projecting from a proximal end 840 of the heat sink 828. The coolant line 852 may form a U-bend 852c proximate to a distal end 844 of heat sink 828 in an analogous manner as shown with respect to U-bend 850c of coolant line 850 in heat sink 818.

In the foregoing embodiment, it is particularly suitable for the coolant lines 850 and 852 to contain an active cooling fluid (e.g., a thermally conductive, non-electrically conductive cooling liquid or a gas, e.g., air). In particular, the cooling fluid may include a liquid coolant such as water or a non-conductive fluid such as a medicinal or biocompatible fluid. However, a gas such as, but not limited to, air, nitrogen or carbon dioxide (preferably at ambient or above ambient pressure conditions) may be applied under forced flow conditions. Alternatively, coolant lines 850 and 852 may also be filled with a stagnant substance such as a below ambient temperature gas (including air, nitrogen or carbon dioxide), or a liquid or solid or frozen substance such as water ice or dry ice (solid carbon dioxide).

Coolant applied to coolant supply lines 850 and 852 removes the heat Q generated during the tissue sealing process. As discussed in more detail below with respect to FIGS. 14A and 14B, the heat sinks 818 and 828 may be configured to be coupled to an ultimate heat sink for transferring heat from the jaw members 710 and 720. More particularly, via the coolant supply ends 850a, 852a, the coolant or cooling lines 850 and 852 may be configured to receive the coolant to transfer the heat from the respective thermoelectric cooling plates 718 and 728. Furthermore, via the coolant return ends 850b, 852b, the coolant or cooling lines 850 and 852 may be configured to be coupled to an ultimate heat sink via the forceps 10.

Figure 11:
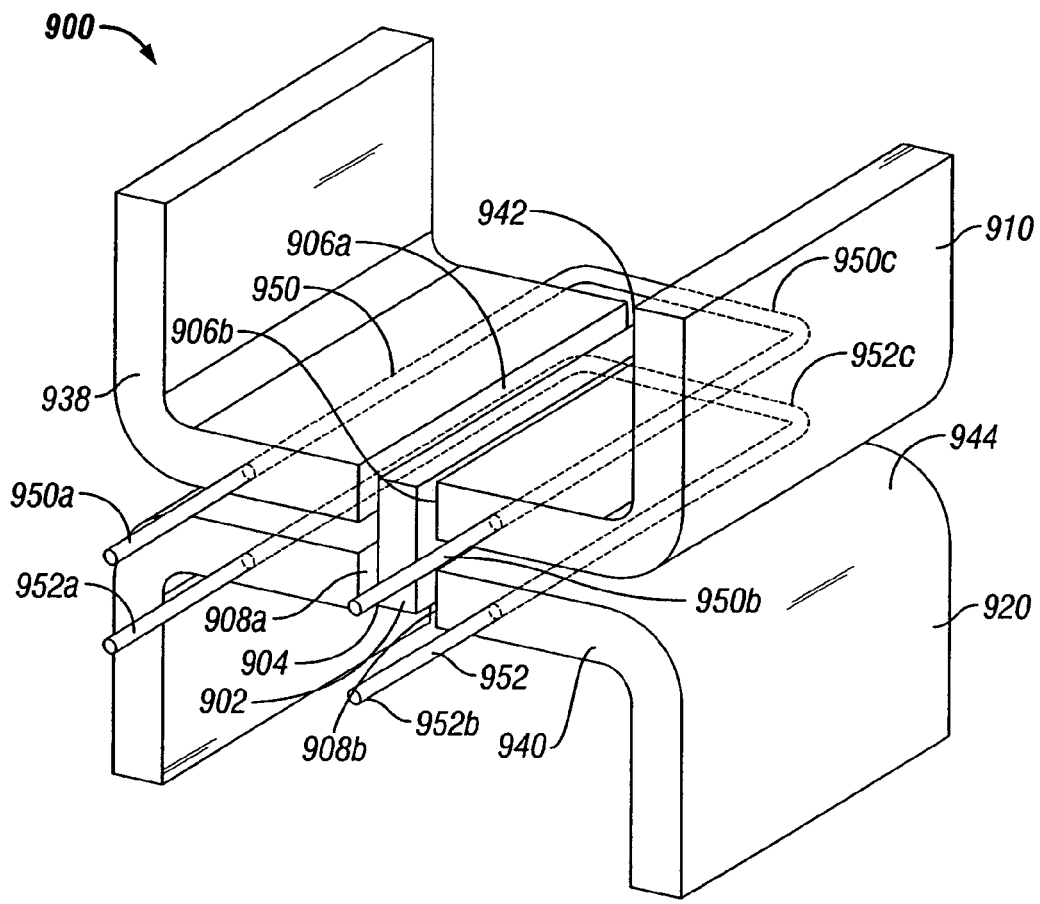
FIG. 11 shows a perspective view of the jaw members of an electrode sealing assembly which are configured to support yet another alternate embodiment of an electrode cooling assembly according to the present disclosure.

FIG. 11 shows yet another embodiment of an electrode cooling system for an electrode assembly 900 according to the present disclosure. More particularly, FIG. 11 shows a proximal end 938 of an upper electrode jaw member 910 and a proximal end 940 of a lower electrode jaw member 920 of electrode assembly 900 adapted to bipolar forceps 10. A knife blade 902 is shown disposed within a knife slot 904 formed by the inward lateral side edges 906a and 906b of the upper jaw member 910 and by the inward lateral side edges 908a and 908b of the lower jaw member 920. The jaw members 910 and 920 have a generally U-shaped cross-section.

At least one of the jaw members 910 and 920 includes a cooling line disposed therethrough or embedded therein. More particularly, a coolant or cooling line 950 may be disposed or embedded within upper electrode jaw member 910. The coolant line 950 has a coolant supply end 950a and a coolant return end 950b projecting from a proximal end 938 of the upper jaw member 910. The coolant line 950 may form a U-bend 850c proximate to a distal end 942 of upper jaw member 910.

Similarly, a coolant or cooling line 952 may be disposed or embedded within lower electrode jaw member 920. The coolant line 952 has a coolant supply end 952a and a coolant return end 952b projecting from a proximal end 940 of the lower jaw member 920. The coolant line 952 may form a U-bend 952c proximate to a distal end 944 of lower jaw member 920.

The coolant lines 950 and 952 may be configured to receive a coolant to transfer heat from jaw members 910 and/or 920. In a similar manner to the previous embodiment described above, it is particularly suitable for the coolant received by the coolant lines 950 and 952 to be an active cooling fluid (preferably, a non-electrically conductive cooling liquid or a gas, e.g., air).

Coolant applied to coolant supply lines 950 and 952 removes the heat Q generated during the tissue sealing process. As discussed in more detail below with respect to FIGS. 14A and 14B, the coolant supply ends 950a, 952a and coolant return ends 950b, 952b may be coupled to an ultimate heat sink via the forceps 10.

Figure 12:
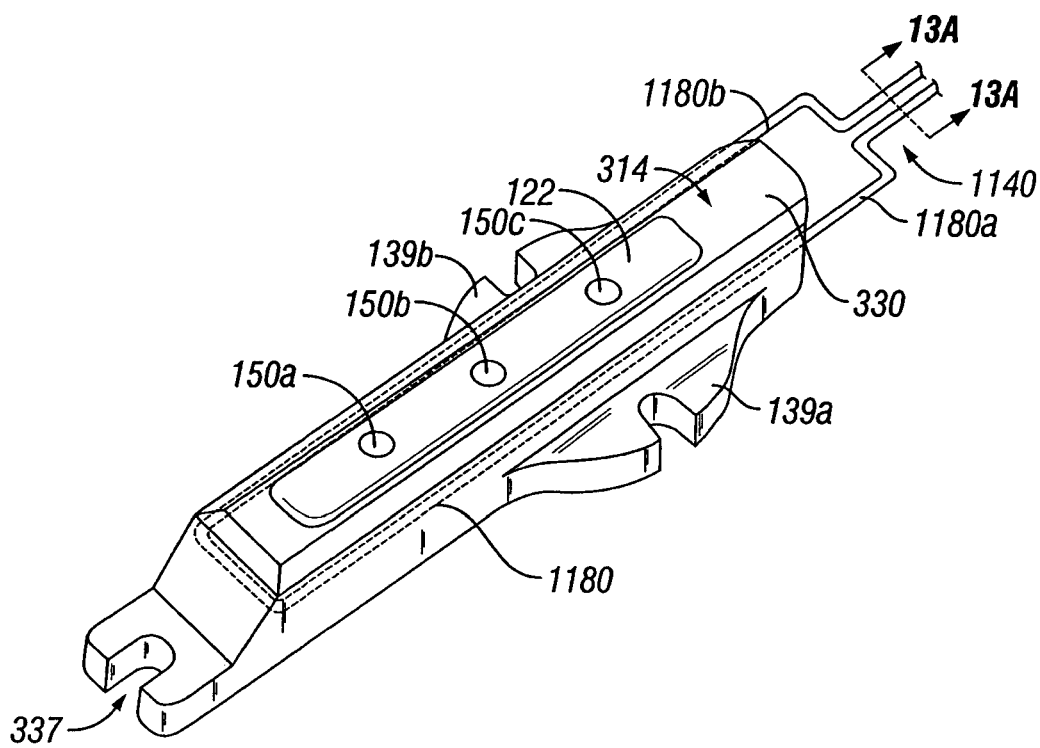
FIG. 12 is an enlarged, perspective view of yet another alternate embodiment of the electrode sealing assembly of FIG. 4 showing an active cooling system designed to reduce thermal spread during activation.

FIG. 12 is an enlarged, perspective view of still another embodiment of the electrode sealing assembly of FIG. 4. More particularly, FIG. 12 shows yet another possible configuration of the lower jaw member 320 of the electrode sealing assembly 100 (or 100') designed to reduce thermal spread to adjacent tissue. This embodiment is in all respects identical to the embodiment disclosed by FIG. 4 except that open active cooling system 340 with a common supply line 355, which branches out into coolant lines 355a and 355b to supply coolant 370 through the series of nozzles or ports 350a and 350b located on an upper surface 330 of the insulating housing 314, is replaced by closed active coolant system 1140 which includes a U-shaped continuous coolant loop 1180 having a coolant supply end 1180a and a coolant return end 1180b. The coolant supply loop 1180 is disposed through or embedded within the insulating housing 314 surrounding the sealing plate 122. The coolant loop 1180 is configured to receive the coolant 370, which is, typically, a non-electrically conductive cooling liquid or gas (e.g., air) such as previously described. The active coolant 370 is caused to flow through the coolant loop 1180 to reduce heat dissipation to surrounding tissue which is generated by the tissue sealing process in sealing plate 122. As is the case of the embodiment of FIG. 4, a thermally conductive material is not utilized as the heat absorbing material or heat sink, but, rather, the active cooling system 1140 surrounds the sealing plate 122. As is discussed in more detail later with respect to FIGS. 14A and 14B, the coolant loop 1180 transports the coolant to an ultimate heat sink for dissipating heat away from surrounding tissue.

With respect to this particular embodiment and compared to the embodiments of FIGS. 2A, 2B, 3 and 4, again, the insulating housing 314 encapsulates the sealing plate 122 by virtue of a mechanical connection or manufacturing process, e.g. stamp molding or injection molding.

Figure 13A:
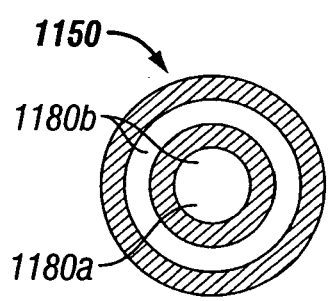
FIG. 13A is a cross-sectional end view of an embodiment of a cooling line for an electrode cooling assembly.

FIG. 13A is a cross-sectional end view of one embodiment of cooling loop 1180 for the electrode cooling assemblies of FIG. 12. More particularly, the ends 1180a and 1180b of the cooling loop 1180 are joined together in a common cooling line 1150. The common cooling line 1150 includes typically an inner tubular shaped conduit which can function as either supply line 1180a or return line 1180b, and an outer concentrically arranged tubular shaped conduit which can function conversely as either return line 1180b or supply line 1180a, respectively.

Figure 13B:
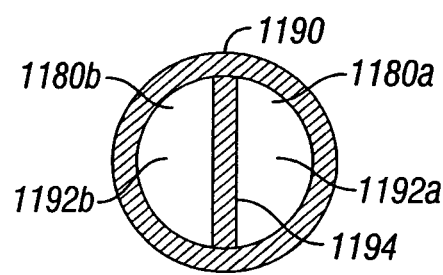
FIG. 13B is a cross-sectional end view of an alternate embodiment of a cooling line for an electrode cooling assembly.

FIG. 13B is a cross-sectional end view of an alternate embodiment of a cooling line for the electrode assemblies of FIG. 12. More particularly, in a similar manner to the embodiment of FIG. 13A, the ends 1180a and 1180b of the cooling loop 1180 are again joined in a common cooling line designated as 1190. However, the common cooling line 1190 includes a generally tubular configuration which is segmented into two inner flow channels 1192a and 1192b via a partition 1194. The inner flow channel 1192a can function as either supply line 1180a or return line 1180b, while conversely, the inner flow channel 1192b can function as either return line 1180b or supply line 1180a, respectively.

Those skilled in the art will recognize that the coolant loops 850 and 852, and 950 and 952 (see FIGS. 10A, 10B and 11) may be configured in an analogous manner as common cooling lines 1150 and 1190.

Figure 14A:
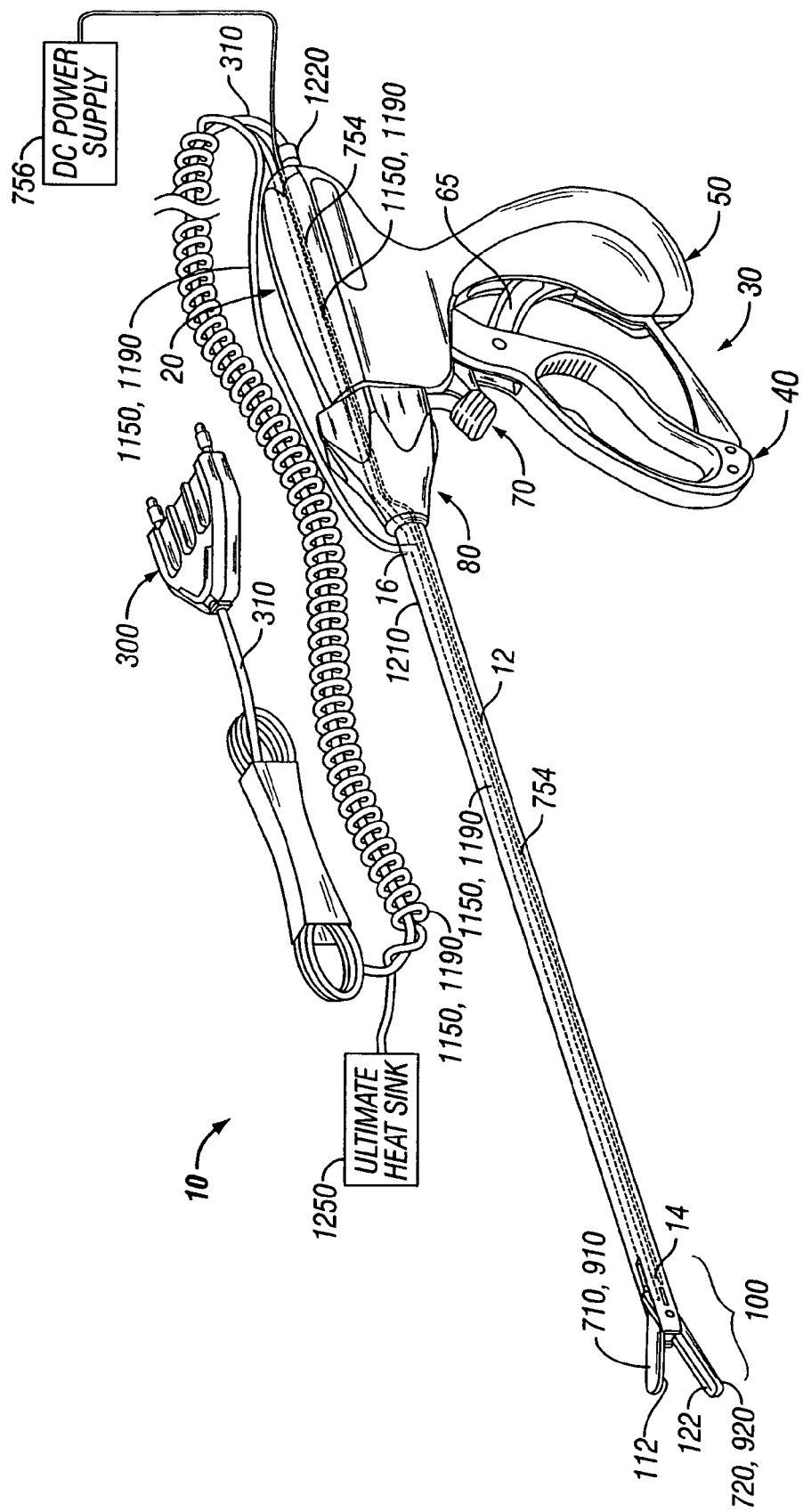
FIG. 14A is a perspective view of the endoscopic bipolar forceps of FIG. 1A which is configured to support the cooling lines of FIG. 4, FIG. 10A, FIG. 10B, FIG. 11, and FIG. 12.

FIG. 14A is a perspective view of the endoscopic bipolar forceps of FIG. 1A which is configured to support the common cooling lines 1150 and 1190 (see FIG. 12, FIG. 13A and FIG. 13B). More particularly, the forceps 10 includes the shaft 12 which has a distal end 14 dimensioned to mechanically engage the end effector assembly 100 and a proximal end 16 which mechanically engages the housing 20 proximate the rotating assembly 80. The cooling line 1150, or 1190 extends from the upper and lower jaws, e.g., jaw members 710, 720, 910, 920 through the shaft 12 and through the housing 20 at a port 1210 proximate the shaft 12 from which the cooling line 1150, or 1190 emerges at a port 1220 in the housing 20 proximate the electrosurgical cable 310. Alternatively, the cooling line 1150, or 1190, may be configured to bypass the housing 20 and only emerges from the shaft 12 at port 1210. Typically, in either embodiment, the cooling line 1150 or 1190 is coiled around the electrosurgical cable 310 to a convenient point at which it is directed to an ultimate heat sink 1250. The cable 754 which provides DC power to the TEC plates 718 and 728 as previously described extends from the TEC plates 718 and 728 through the shaft 12 and through the housing 20 from which cable 754 emerges at port 1220 (or a separate port) to connect to the DC power supply 756. It is contemplated that the forceps 10 described with respect to FIG. 14A and as follows in FIG. 14B may be utilized with any of the aforementioned end effector assemblies and jaw members described herein.

Figure 14B:
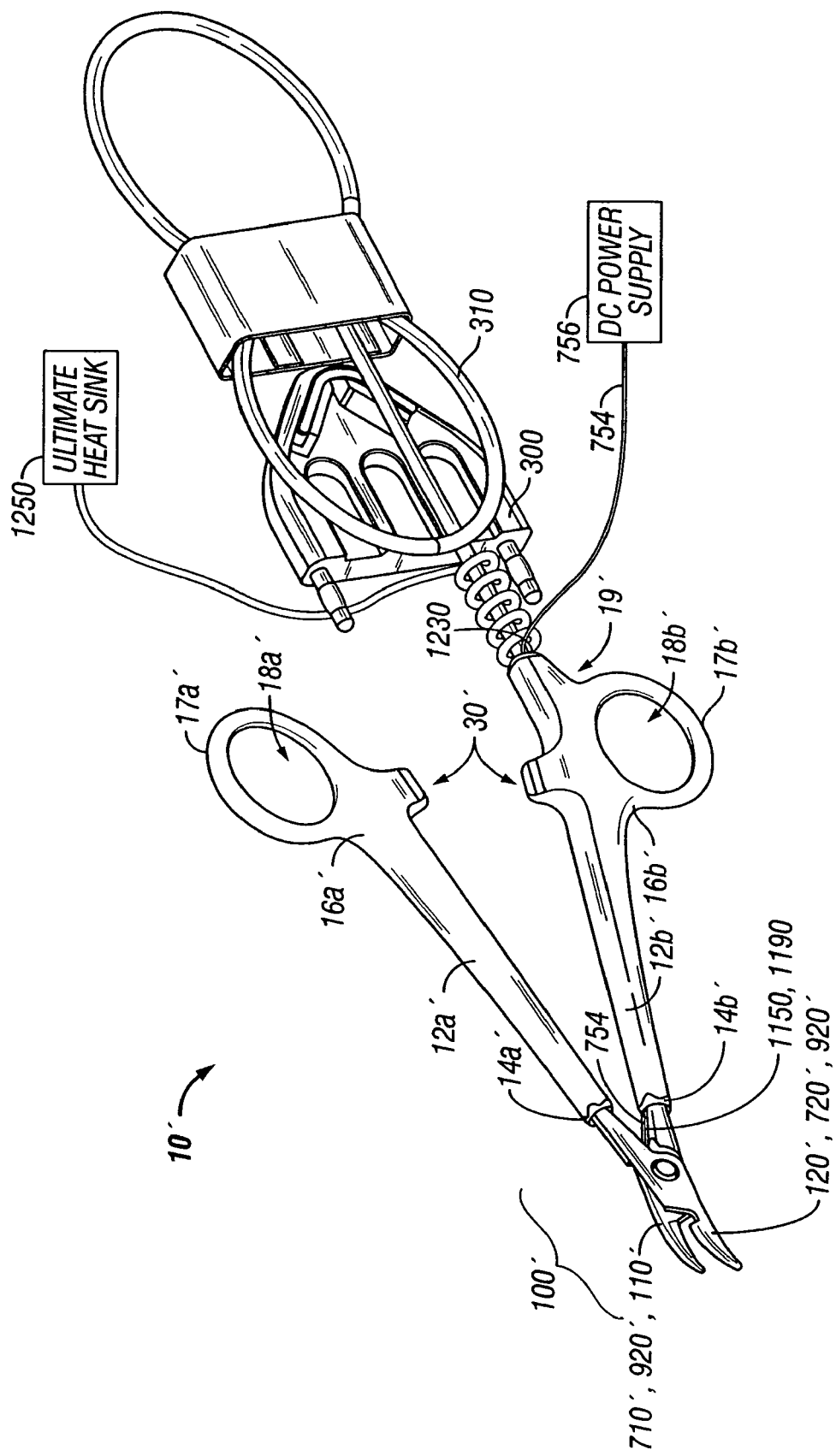
FIG. 14B is a perspective view of the open bipolar forceps of FIG. 1B which is configured to support the cooling lines of FIG. 4, FIG. 10A, FIG. 10B, FIG. 11, and FIG. 12.

More particularly, FIG. 14B is a perspective view of the open bipolar forceps of FIG. 1B which is configured to support the cooling line of FIG. 10, FIG. 11B and FIG. 11C. As disclosed previously with respect to FIG. 1B, open forceps 10' includes a pair of elongated shaft portions 12a', 12b' each having a proximal end 16a' and 16b', respectively, and a distal end 14a' and 14b', respectively. The forceps 10' includes jaw assembly 100' which attaches to the distal ends 14a' and 14b' of shafts 12a' and 12b', respectively. Jaw assembly 100' includes an upper jaw member 710' or 910' and a lower jaw member 720' or 920' which are movable relative to one another to grasp tissue therebetween. Those skilled in the art will recognize that upper jaw members 710' and 910' are substantially identical to upper jaw member 710 and 910, respectively, except for being configured to adapt to the open forceps 10'. Similarly, those skilled in the art will recognize that lower jaw members 720' and 920' are substantially identical to upper jaw member 720 and 920, respectively, except for being configured to adapt to the open forceps 10'.

Each shaft 12a' and 12b' includes a handle 17a' and 17b' disposed at the proximal end 16a' and 16b' thereof which each define a finger hole 18a' and 18b', respectively, therethrough for receiving a finger of the user. As can be appreciated, finger holes 18a' and 18b' facilitate movement of the shafts 12a' and 12b' relative to one another which, in turn, pivot the jaw members 110' and 120' from the open position wherein the jaw members 110' and 120' are disposed in spaced relation relative to one another for manipulating tissue to a clamping or closed position wherein the jaw members 110' and 120' cooperate to grasp tissue therebetween.

One of the shafts, e.g., 12b', includes a proximal shaft-connector/flange 19' which is designed to connect the forceps 10' to a source of RF energy (not shown) via an electrosurgical cable 310 and plug 300. Although the details relating to the inner-working electrical connections and various components of forceps 10' are disclosed in commonly-owned U.S. patent application Ser. No. 10/369,894 which is incorporated in its entirety by reference herein, it is disclosed herein that cooling line 1150 or 1190 and electrical cable 754 extends from the upper and lower jaw members 110' and 120' through the shaft 12b' to the proximal shaft/connector flange 19' which interfaces with electrosurgical cable 310. The cooling line 1150 or 1190 emerges from the flange 19' at a port 1230 proximate the power cord 310. Typically, the cooling line 1150 or 1190 is coiled around the electrosurgical cable 310 to a convenient point at which it is directed to the ultimate heat sink 1250. The electrical cable 754 emerges at the port 1230 from which it extends to connect to DC power supply 756.

From the foregoing and with reference to the various figure drawings, those skilled in the art will appreciate that certain modifications can also be made to the present disclosure without departing from the scope of the same. For example, although it is preferable that jaw members 110 and 120 meet in parallel opposition, and, therefore, meet on the same plane, in some cases it may be preferable to slightly bias the jaw members 110 and 120 to meet each other at the distal end such that additional closure force on the handles is required to deflect the electrodes in the same plane. It is envisioned that this could improve seal quality and/or consistency. Alternatively, the jaws members 110 and 120 may be configured to close in a heel-based manner or in an independently floating (with respect to parallel) fashion.

It is envisioned that while the jaw members 710, 710', 910, 910' and 720, 720', 920, 920' are configured for dissipating heat generated by electrosurgical RF power, the cooling members disclosed herein (i.e., thermoelectric plates 718 and 728, corresponding heat sinks 818 and 828 and the cooling lines 850, 852, 950, 952; and the cooling loops 340, 1150 and 1190 for cooling the insulating housing 314) may be adapted as well to other heating modalities. Such other heating modalities include, but are not limited to, ultrasonic, capacitive or thermoelectric heating power sources.

While various embodiments of the disclosure have been described, it is not intended that the disclosure be limited thereto, as it is intended that the disclosure be as broad in scope as the art will allow and that the specification be read likewise. Therefore, the above descriptions should not be construed as limiting, but merely as exemplifications of preferred embodiments. Those skilled in the art will envision other modifications within the scope and spirit of the claims appended hereto.

What is claimed is:

1. An electrode sealing assembly designed for use with an electrosurgical instrument for sealing tissue, comprising:
   first and second jaw members being movable from a first position in spaced relation relative to one another to at least one second position for grasping tissue therebetween, the jaw members including:
   electrically conductive sealing plates disposed in opposing relation to one another, at least one jaw member including:
   a thermoelectric cooling plate having a first surface in direct contact with an outer surface of the sealing plate, said thermoelectric cooling plate including first and second electrical connections disposed on opposite sides of the thermoelectric cooling plate, said first connection being configured to selectively transmit a first electrical potential and said second connection being configured to selectively transmit a second electrical potential such that heat generated by the sealing plates is transferred away from the tissue via the thermoelectric cooling plate,
   wherein the at least one jaw member further includes a heat sink disposed in direct contact with a second surface of the thermoelectric cooling plate, and
   wherein the heat sink is made from a thermally conductive, electrically insulative cool polymer.

2. An electrode sealing assembly according to claim 1, wherein the heat sink is configured to be coupled to a second heat sink for transferring heat at least one of to and from the jaw member.

3. An electrode sealing assembly according to claim 2, wherein the second heat sink is made from a thermally conductive, electrically insulative cool polymer.

4. An electrode sealing assembly according to claim 1, wherein the heat sink includes a coolant line disposed therethrough.

5. An electrode sealing assembly according to claim 4, wherein the coolant line is configured to receive a coolant to transfer heat from the thermoelectric cooling plate.

6. An electrode sealing assembly according to claim 5, wherein the coolant is a thermally conductive, non-electrically conductive fluid.

7. An electrode sealing assembly according to claim 6, wherein the non-electrically conductive fluid is one of the group consisting of air, nitrogen and carbon dioxide.

8. An electrode sealing assembly according to claim 5, wherein the coolant is a medicinal fluid.

\* \* \* \* \*